United States Patent
Hiroshige et al.

(10) Patent No.: US 10,206,647 B2
(45) Date of Patent: Feb. 19, 2019

(54) RADIOGRAPHIC IMAGE CAPTURING DEVICE AND RADIOGRAPHIC IMAGE CAPTURING SYSTEM

(71) Applicant: KONICA MINOLTA, INC., Chiyoda-ku, Tokyo (JP)

(72) Inventors: Akira Hiroshige, Kokubunji (JP); Hidetake Tezuka, Tachikawa (JP); Shintaro Muraoka, Hachioji (JP)

(73) Assignee: KONICA MINOLTA, INC., Tokyo (JP)

( * ) Notice: Subject to any disclaimer, the term of this patent is extended or adjusted under 35 U.S.C. 154(b) by 219 days.

(21) Appl. No.: 15/207,890

(22) Filed: Jul. 12, 2016

(65) Prior Publication Data

US 2017/0014094 A1 Jan. 19, 2017

(30) Foreign Application Priority Data

Jul. 17, 2015 (JP) .................................. 2015-142809

(51) Int. Cl.
*A61B 6/00* (2006.01)
*H04N 5/232* (2006.01)
(Continued)

(52) U.S. Cl.
CPC .................. *A61B 6/54* (2013.01); *A61B 6/42* (2013.01); *A61B 6/4233* (2013.01);
(Continued)

(58) Field of Classification Search
CPC .................................................... A61B 6/542
See application file for complete search history.

(56) References Cited

U.S. PATENT DOCUMENTS 9,737,271 B2* 8/2017 Iwashita ............... A61B 6/4208
2014/0209806 A1* 7/2014 Nishino ............... A61B 6/4007
250/363.01

FOREIGN PATENT DOCUMENTS

| JP | 2004312434 A | 11/2004 |
|---|---|---|
| JP | 2011235006 A | 11/2011 |
| WO | 2009090894 A1 | 7/2009 |

OTHER PUBLICATIONS

International Preliminary Report on Patentability (IPRP) dated Jan. 23, 2018 issued in counterpart International Application No. PCT/JP2016/057708.

(Continued)

*Primary Examiner* — Dani Fox
(74) *Attorney, Agent, or Firm* — Holtz, Holtz & Volek PC

(57) ABSTRACT

A radiographic image capturing device includes the following. A two-dimensional array of radiation detectors generate electrical charges corresponding to a dose of incident radiation. A control unit reads the electrical charges discharged from the radiation detectors in a form of image data. The control unit has radiographic modes including a still image mode for still image radiography, a moving image mode for moving image radiography, and a continuous radiographic mode for reading the image data without distinguishing between the still image radiography and the moving image radiography. The control unit selects the continuous radiographic mode to sequentially read the image data when an instruction on performing the still image radiography or the moving image radiography is not sent from an external control device or a user or when the radiographic mode is unknown due to communication failure with the external control device.

8 Claims, 12 Drawing Sheets

(51) Int. Cl.
  *H04N 5/32*    (2006.01)
  *H04N 5/361*   (2011.01)
  *H04N 5/378*   (2011.01)

(52) U.S. Cl.
  CPC ............. *A61B 6/4405* (2013.01); *A61B 6/46* (2013.01); *A61B 6/467* (2013.01); *A61B 6/5205* (2013.01); *A61B 6/586* (2013.01); *H04N 5/23245* (2013.01); *H04N 5/32* (2013.01); *H04N 5/361* (2013.01); *H04N 5/378* (2013.01)

(56) References Cited

OTHER PUBLICATIONS

International Search Report dated Jun. 7, 2016 issued in counterpart International Application No. PCT/JP2016/057708.

* cited by examiner

FIG.10
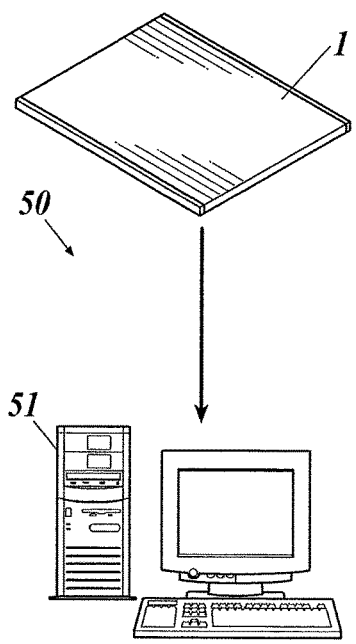
FIG.11
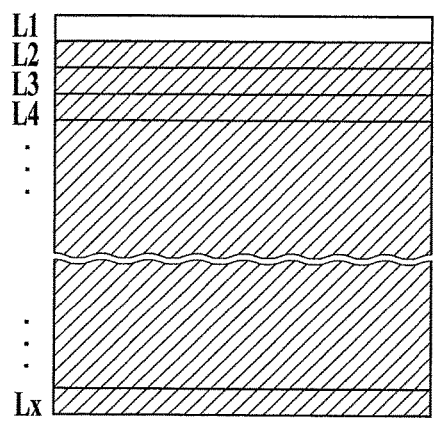
m-th FRAME
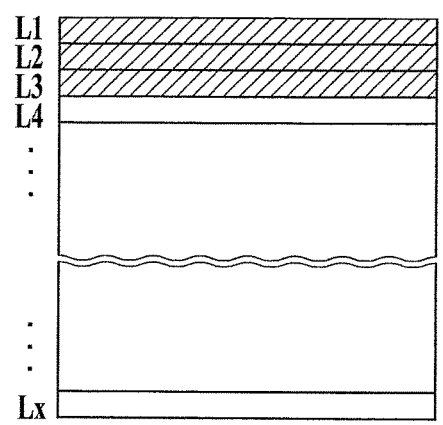
(m+1)-th FRAME

RADIOGRAPHIC IMAGE CAPTURING DEVICE AND RADIOGRAPHIC IMAGE CAPTURING SYSTEM

BACKGROUND OF THE INVENTION

Field of the Invention

The present invention relates to a radiographic image capturing device and a radiographic image capturing system.

Description of Related Art

Various radiographic image capturing devices (flat panel detectors) have been developed that include two-dimensional arrays of radiographic detectors and read the electrical charges generated at the radiographic detectors in response to radiation emitted from irradiators through subjects, as image data. Such radiographic image capturing devices are used in medical facilities, such as hospitals. Portable radiographic image capturing devices have also been developed and put to practical use that include casings accommodating sensor panels provided with radiographic detectors.

Similar to traditional silver halide films and computed radiographic (CR) cassettes accommodating photostimulable phosphor sheets, such a radiographic image capturing device can perform still image radiography for capturing still images (simple radiography or general radiography) by emitting radiation once and irradiating the radiographic image capturing device with radiation while the subject is disposed in front of the radiographic image capturing device.

The traditional silver halide films and CR cassettes undergo double-exposure or multi-exposure when irradiated multiple times with radiation while the subjects are disposed in front of the traditional silver halide films and CR cassettes. In contrast, the radiographic image capturing device can capture multiple radiographic images by multiple exposures with radiation with a subject disposed in front of the radiographic image capturing device, because the radiographic image capturing device can transfer the data of the captured radiographic images (i.e., image data) to external units or store the image data in a storage unit provided in the radiographic image capturing device.

Unlike traditional silver halide films and CR cassettes, the radiographic image capturing device can also capture moving images composed of consecutive frames of radiographic images (moving image radiography), such as in kymographic radiography for capturing the dynamic state of pulmonary ventilation or pulmonary blood flow of a patient having a pulmonary disorder (for example, refer to Japanese Patent Application Laid-Open No. 2004-312434 and WO2009/090894) or tomosynthetic radiography for capturing multiple radiographic images of a subject while moving the irradiator and the radiographic image capturing device.

Such moving image radiography differs from regular videography by a video camera and should be understood as a form of limited videography. The moving image radiography according to the present invention refers to the capturing of multiple consecutive frames of radiographic images that collectively appear as a moving image, and often has a frame rate smaller than regular videography, which has a frame rate of 30 frames per second, and a limited duration. In regular videography, the captured video images are usually displayed in real-time, whereas in the moving image radiography, such as kymographic and tomosynthetic radiography, real-time display of the moving images is not always supported and in many cases a moving image is not (or cannot be) displayed simultaneously with the image capturing.

The present invention is described with terms associated with video images and videography. These terms, however, do not refer to regular video images captured by video cameras and regular videography but to multiple frames of consecutive radiographic images.

For example, in kymographic radiography, pulsed radiation is emitted from the irradiator or a low dose of radiation is continuously emitted from the irradiator. In the pulsed radiation, the radiographic image capturing device usually reads image data in synchronization with the emission timing of the radiation from the irradiator, whereas in the low-dose radiation, the timing of reading of the image data is appropriately controlled for image capturing.

The radiographic image capturing device can capture still images and moving images. Thus, as known in the field of digital cameras, for example, the radiographic image capturing device may be provided with a selection switch that can be operated by the user or radiologist to switch between two radiographic modes, i.e., a still image mode for still image radiography and a moving image mode for moving image radiography. Alternatively, a signal may be sent from an external controller, such as a console, to the radiographic image capturing device to switch the radiographic mode of the radiographic image capturing device between the still image mode and the moving image mode.

In a barium meal test, for example, the subject is continuously irradiated with low-dose radiation to observe the condition of the stomach in the moving image mode, and the radiographic mode is switched to the still image mode at timings instructed by the radiologist to capture still images (for example, refer to Japanese Patent Application Laid-Open No. 2011-235006).

In the case described above, the radiographic image capturing device is switched between the still image mode and the moving image mode through operation of a selection switch of the radiographic image capturing device by the operator or radiologist or operation of an external controller, such as a console, by the operator, to send a signal instructing the switching of the radiographic mode to the radiographic image capturing device.

Alternatively, the radiographic mode of the radiographic image capturing device can be automatically switched between the still image mode and the moving image mode with a control unit of the radiographic image capturing device on the basis of radiography order information that assigns still image radiography or moving image radiography (or radiography order information that assigns the site to be captured, thereby assigning the still image radiography or the moving image radiography) downloaded to the console from an external system, such as a radiology information system (RIS), in response to an instruction from the operator or radiologist and sent to the radiographic image capturing device, directly input to the console by the operator and sent to the radiographic image capturing device, or directly input to the radiographic image capturing device by the operator.

The radiographic image device carries out the procedures for radiography corresponding to the selected radiographic mode, i.e., the procedure for capturing still images in the still image mode or the procedure for capturing moving images in the moving image mode. In either mode, the radiographic image capturing device should preliminarily identify whether the image capturing to be performed is still image radiography or moving image radiography on the basis of the operation by the radiologist or the inputted radiography order information.

For example, in the radiography performed on a patient in a hospital room or the home of a patient with a portable radiographic image capturing device and a portable irradiator, radiography performed to triage patients at an accident site or a disaster site with a portable radiographic image capturing device and a portable irradiator, or radiography performed on an injured race horse on site, the radiographic modes (still image mode and moving image mode) and the order of the radiographic modes often cannot be preliminarily selected.

In such a case, the switching operation of the radiographic modes of the radiographic image capturing device between the still image mode and the moving image mode is troublesome for the operator or radiologist. In another case, radiography may have to be promptly and continuously performed before the radiographic mode (still image mode or moving image mode) can be instructed.

Even if the radiographic image capturing device exchanges signals and data with an external controller, such as a console, via wireless communication and receives radiography order information that assigns still image radiography or moving image radiography from the controller, the radiographic image capturing device cannot maintain communication with the external controller due to an insufficient communication environment with weak signals in some cases. In such cases, the control unit of the radiographic image capturing device cannot determine whether the radiographic mode is a still image mode or a moving image mode.

In this case, the radiographic image capturing device may have a radiographic mode for performing either still image radiography or moving image radiography besides the still image mode for performing still image radiography and the moving image mode for performing moving image radiography. This mode is preferred because it allows the operator or radiologist to freely perform radiography with the radiographic image capturing device without the troublesome operation of selecting a radiographic mode or switching between radiographic modes.

BRIEF SUMMARY OF THE INVENTION

An object of the present invention, which has been conceived to solve the problem described above, is to provide a radiographic image capturing device that can perform both still image radiography and moving image radiography even without an instruction that assigns the radiographic mode (still image mode or moving image mode) from an external controller, such as a console, or a user or radiologist, or the radiographic mode is unknown to be either the still image radiography or the moving image radiography due to interruption in the communication between the radiographic image capturing device and the external controller.

Radiographic still images and the multiple frames of the radiographic moving images based on image data captured by the radiographic image capturing device described above can be appropriately generated only if the image data captured by the radiographic image capturing device is correctly identified as image data of still image radiography or image data of moving image radiography.

Thus, another object of the present invention is to provide a radiographic image capturing device or a radiographic image capturing system that can correctly identify the image data captured by the radiographic image capturing device as image data of still image radiography or image data of moving image radiography.

According to an aspect of the present invention, there is provided a radiographic image capturing device including: a two-dimensional array of radiation detectors that generate electrical charges corresponding to a dose of incident radiation; and a control unit that reads the electrical charges discharged from the radiation detectors in a form of image data, wherein, the control unit has radiographic modes including a still image mode for still image radiography, a moving image mode for moving image radiography, and a continuous radiographic mode for reading the image data without distinguishing between the still image radiography and the moving image radiography, and the control unit selects the continuous radiographic mode to sequentially read the image data of individual frames when an instruction on performing the still image radiography or the moving image radiography is not sent from an external control device or a user or when the radiographic mode is unknown to be either the still image radiography or the moving image radiography due to communication failure with the external control device.

According to another aspect of the present invention, there is provided a radiographic image capturing system including: the radiographic image capturing device; and an image processor, wherein the image processor in the continuous radiographic mode determines whether the image data of the individual frames transmitted from the radiographic image capturing device directly or indirectly via an external unit is image data of the still image radiography or image data of the moving image radiography on the basis of a value of the image data or on the basis of at least one of irradiation time from the start of irradiation of radiation to the end of the irradiation radiation, a time interval between the end of the irradiation of radiation and the start of the next irradiation of radiation, and a dose rate of the emitted radiation, determined through analysis of the image data.

A radiographic image capturing device according to the present invention can perform either still image radiography or moving image radiography even without an instruction that assigns the radiographic mode (still image mode or moving image mode) from an external controller, such as a console, or a user or radiologist, or the radiographic mode is unknown to be either the still image radiography or the moving image radiography due to communication failure with the external controller.

The radiographic image capturing device according to the present invention can correctly identify the image data captured by the radiographic image capturing device as image data of still image radiography or image data of moving image radiography.

BRIEF DESCRIPTION OF THE DRAWINGS

The present invention will become more fully understood from the detailed description given hereinbelow and the appended drawings, and thus are not intended to define the limits of the present invention.

FIG. 10 illustrates the configuration of a radiographic image capturing system according to an embodiment.

FIG. 11 schematically illustrates the range of useful image data read when radiation is emitted in the timing illustrated in FIG. 7 in a continuous radiographic mode.

DETAILED DESCRIPTION OF PREFERRED EMBODIMENTS

A radiographic image capturing device and a radiographic image capturing system according to embodiments of the present invention will now be described with reference to the accompanying drawings.

An indirect radiographic image capturing device will now be described that includes a scintillator that converts incident radiation to light having other wavelengths, such as visible light, and acquires image data with radiation detectors. Alternatively, the present invention may be applied to a direct radiographic image capturing device that directly detects incident radiation with radiation detectors without a scintillator.

[Radiographic Image Capturing Device]

Figure 1:
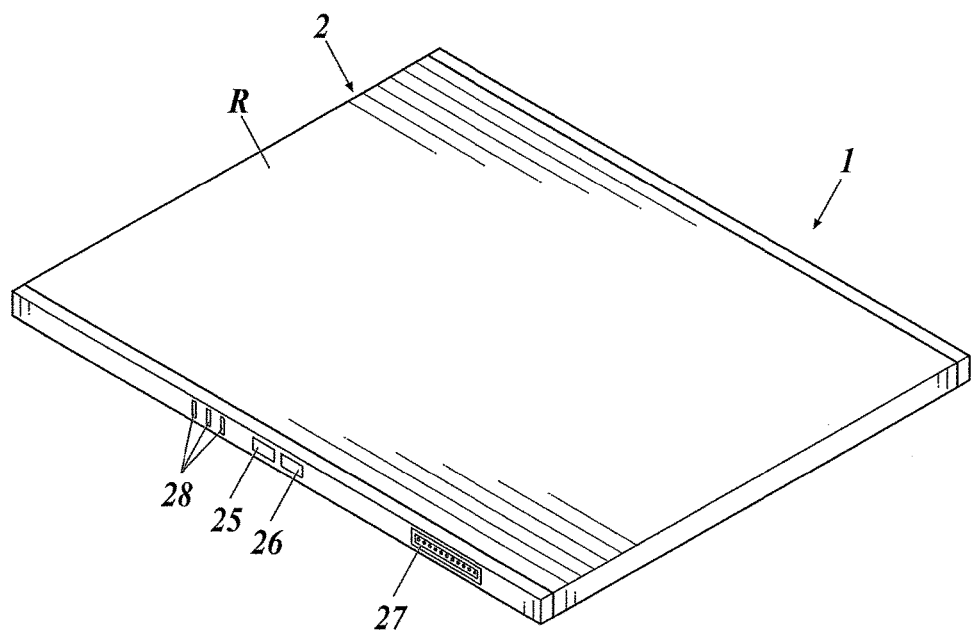
FIG. 1 is an external perspective view illustrating a radiographic image capturing device according to an embodiment.

The basic configuration of a radiographic image capturing device according to this embodiment will now be described. FIG. 1 is an external perspective view of the radiographic image capturing device.

A radiographic image capturing device 1 according to this embodiment includes a casing 2 accommodating radiation detectors 7 and other components as described below. The casing 2 is provided with a power switch 25, a selection switch 26, a connector 27, and an indicator 28 including LEDs on its one side face. Although not illustrated, the casing 2 according to this embodiment is provided with an antenna 29 (see FIG. 2) for wireless communication with external units, for example, on the opposite side face. The radiographic image capturing device 1 uses an antenna 29 for wireless communication with external units. A cable (not shown) can be connected to the connector 27 to establish wired communication with an external unit.

Figure 2:
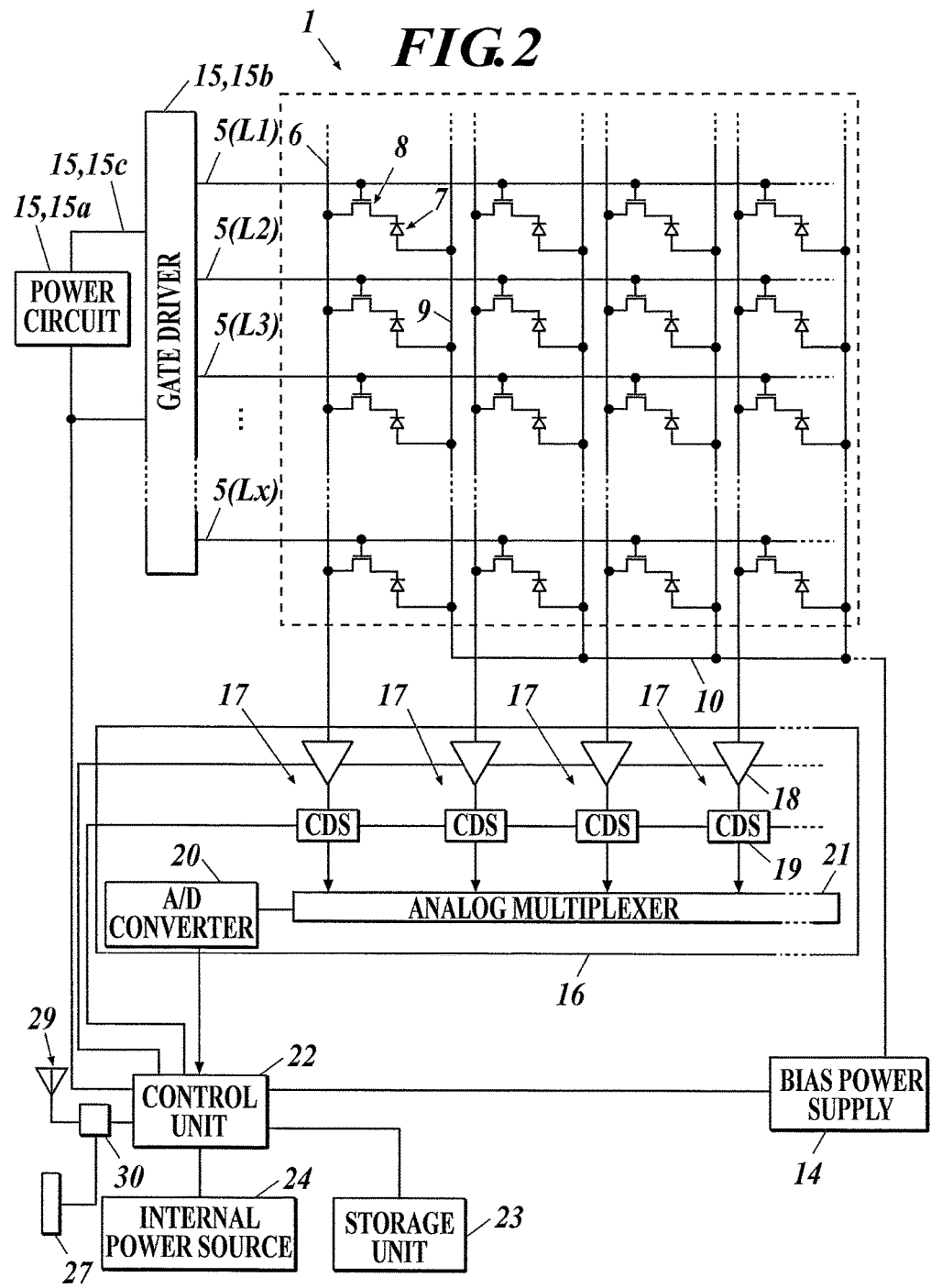
FIG. 2 is a block diagram illustrating an equivalent circuit of the radiographic image capturing device.

FIG. 2 is a block diagram illustrating the equivalent circuit of the radiographic image capturing device. With reference to FIG. 2, multiple radiation detectors 7 are disposed in a two-dimensional array or matrix on a sensor substrate (not shown) of the radiographic image capturing device 1. The radiation detectors 7 each generate an electrical charge depending on the intensity of the incident radiation. The radiation detectors 7 are connected to respective bias lines 9, which are connected to respective connecting lines 10. The connecting lines 10 are connected to a bias power supply 14. The bias power supply 14 applies an inverse bias voltage to the radiation detectors 7 via the bias lines 9.

The radiation detectors 7 are connected to thin film transistors (TFTs) 8, which serve as switching devices and are connected to respective signal lines 6. In a scan driver 15, a power circuit 15a supplies ON and OFF voltages to a gate driver 15b via a line 15c. The gate driver 15b switches the ON and OFF voltages applied to lines L1 to Lx of scanning lines 5. The TFTs 8 are turned on in response to an ON voltage applied via the scanning lines 5 and cause the electrical charges accumulated in the radiation detectors 7 to be discharged via the signal lines 6. The TFTs 8 are turned off in response to an OFF voltage applied via the scanning lines 5 to disconnect the radiation detectors 7 and the respective signal lines 6 and cause accumulation of the electrical charges in the radiation detectors 7.

Multiple reader circuits 17 are provided in a reader IC 16 and connected to the respective signal lines 6. During the reading of image data D, electrical charges discharged from the radiation detectors 7 flow into the reader circuits 17 via the signal lines 6, and voltage values corresponding to the electrical charges are output from amplifier circuits 18. Correlated double sampling circuits ("CDSs" in FIG. 2) 19 read the voltage values from the amplifier circuits 18 and output analog image data items D corresponding to the voltage values to the components downstream. The image data items D are sequentially sent to an A/D converter 20 via an analog multiplexer 21, converted to digital image data items D at the A/D converter 20, and then stored in a storage unit 23.

A control unit 22 includes a computer (not shown) provided with a central processing unit (CPU), a read only memory (ROM), a random access memory (RAM), and an input/output interface connected to a bus, and a field programmable gate array (FPGA). The control unit 22 may be composed of a dedicated controller circuit. The control unit 22 is connected to the storage unit 23 provided with a static RAM (SRAM), a synchronous DRAM (SDRAM), and a NAND flash memory, and a communication unit 30 that establishes wireless or wired communication with external units via the antenna 29 and the connector 27.

The control unit 22 is connected to an internal power source 24 that provides the required electrical power to the functional units including the scan driver 15, the reader circuits 17, the storage unit 23, and the bias power supply 14. During the reading of the image data D, the control unit 22 controls the operation of the scan driver 15, the reader circuits 17, and other components as described above to read the electrical charges discharged from the radiation detectors 7 to the signal lines 6 as the image data D at the reader circuits 17 and the other components.

The radiographic image capturing device 1 according to this embodiment can be installed on a platform (not shown) during radiography. Although not illustrated, the radiographic image capturing device 1 may alternatively be used in a stand-alone state without the platform to capture a radiographic image of the subject or patient by placing the device in contact with the patient or between the patient and the bed.

[Radiographic Mode of Radiographic Image Capturing Device]

The radiographic modes that can be selected by the control unit 22 of the radiographic image capturing device 1 according to this embodiment will now be described. In this embodiment, the control unit 22 has three radiographic modes: a still image mode for still image radiography; a moving image mode for moving image radiography; and a continuous radiographic mode for sequentially reading individual frames of the image data D without distinguishing between still image radiography and moving image radiography.

[Still Image Mode]

Figure 3:
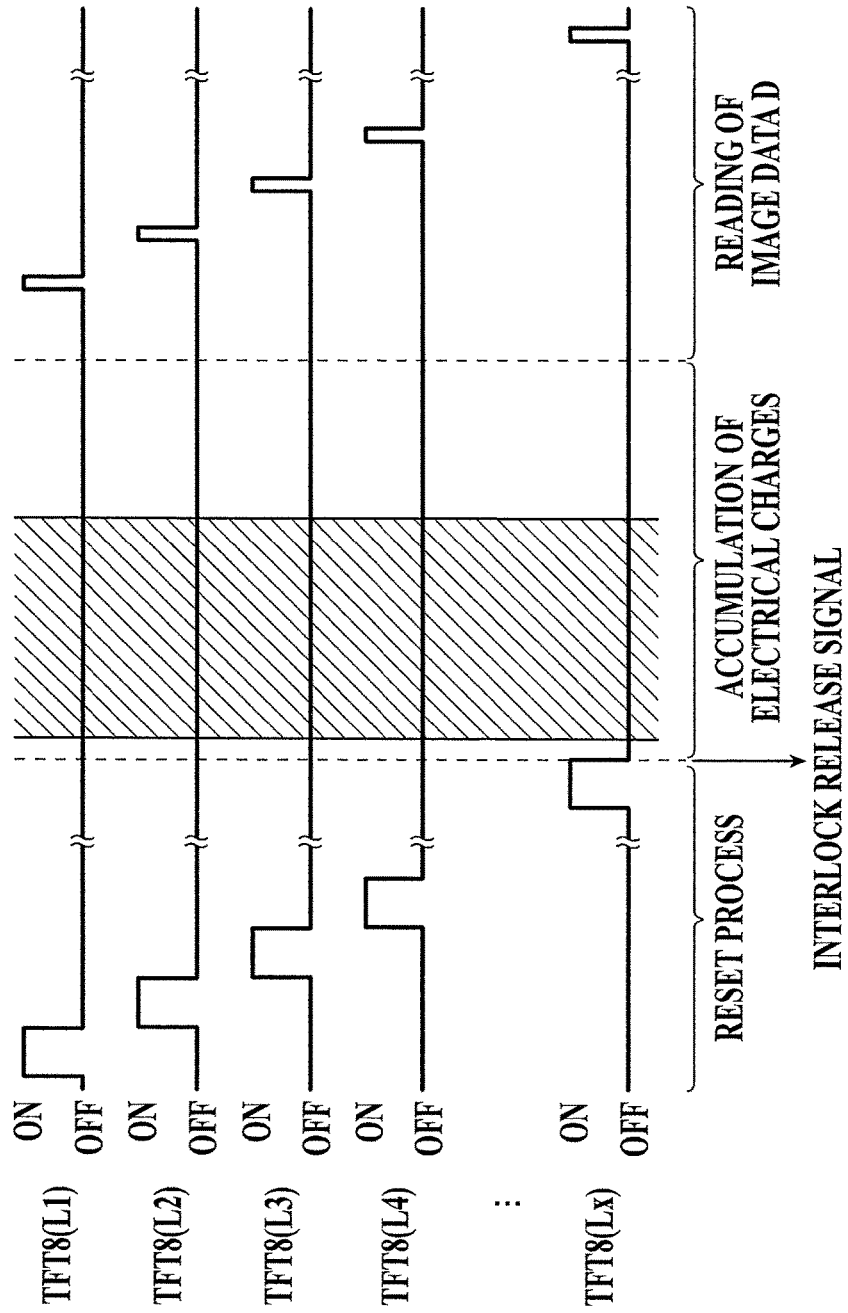
FIG. 3 is a timing chart illustrating the timing of applying an ON voltage to scanning lines during still image radiography performed by the radiographic image capturing device in cooperation with an irradiator.

In the still image mode, the control unit 22 carries out radiography in coordination with an irradiator (not shown), for example. With reference to FIG. 3, the radiation detectors 7 are reset by sequentially applying an ON voltage from a gate driver 15b (see FIG. 2) of the scan driver 15 to the lines L1 to Lx of the scanning lines 5 and discharging the electrical charges remaining in the radiation detectors 7 to the signal lines 6, to remove the remaining electrical charges from the radiation detectors 7.

Upon reception of an irradiation start signal from the irradiator in response to operation of an exposure switch of the irradiator by the operator or radiologist, the control unit 22 of the radiographic image capturing device 1 ends the current reset process of the radiation detectors 7 in response to the application of an ON voltage to the last line Lx of the scanning lines 5, and applies an OFF voltage from the gate driver 15b to the line L1 to Lx of the scanning lines 5 for accumulation of electrical charges, as illustrated in FIG. 3. Simultaneously, an interlock release signal is sent to the irradiator.

Upon reception of an interlock signal from the radiographic image capturing device 1, the irradiator emits radiation. The hatched area in FIG. 3 represents the period of irradiation of radiation. At a predetermined time after the start of the accumulation of electrical charges, the control unit 22 of the radiographic image capturing device 1 sequentially applies an ON voltage from the gate driver 15b to the line L1 to Lx of the scanning lines 5 to read the image data D.

With reference to FIG. 3, in the still image mode, usually, the radiation detectors 7 are reset for accumulation of electrical charges before or after image capturing, without irradiation with radiation of the radiographic image capturing device 1; at a predetermined time after the accumulation of electrical charges, offset data O is read in a similar manner as the reading of image data D.

In the still image mode, radiography is performed without the coordination of the radiographic image capturing device 1 and the irradiator, in some cases. In such a case, the radiographic image capturing device 1 should detect the start of the irradiation of the radiographic image capturing device 1. For example, the radiographic image capturing device 1 may be provided with an X-ray sensor (not shown), and the control unit 22 can detect the start of the irradiation of radiation on the basis of output values from the X-ray sensor, as is well known.

Alternatively, the schemes described in the following publications can be applied to the detection of the start of the irradiation of radiation: Japanese Patent Application Laid-Open No. 2009-219538, WO2011/135917, and WO2011/152093. For the details of the schemes, refer to these publications.

Figure 4:
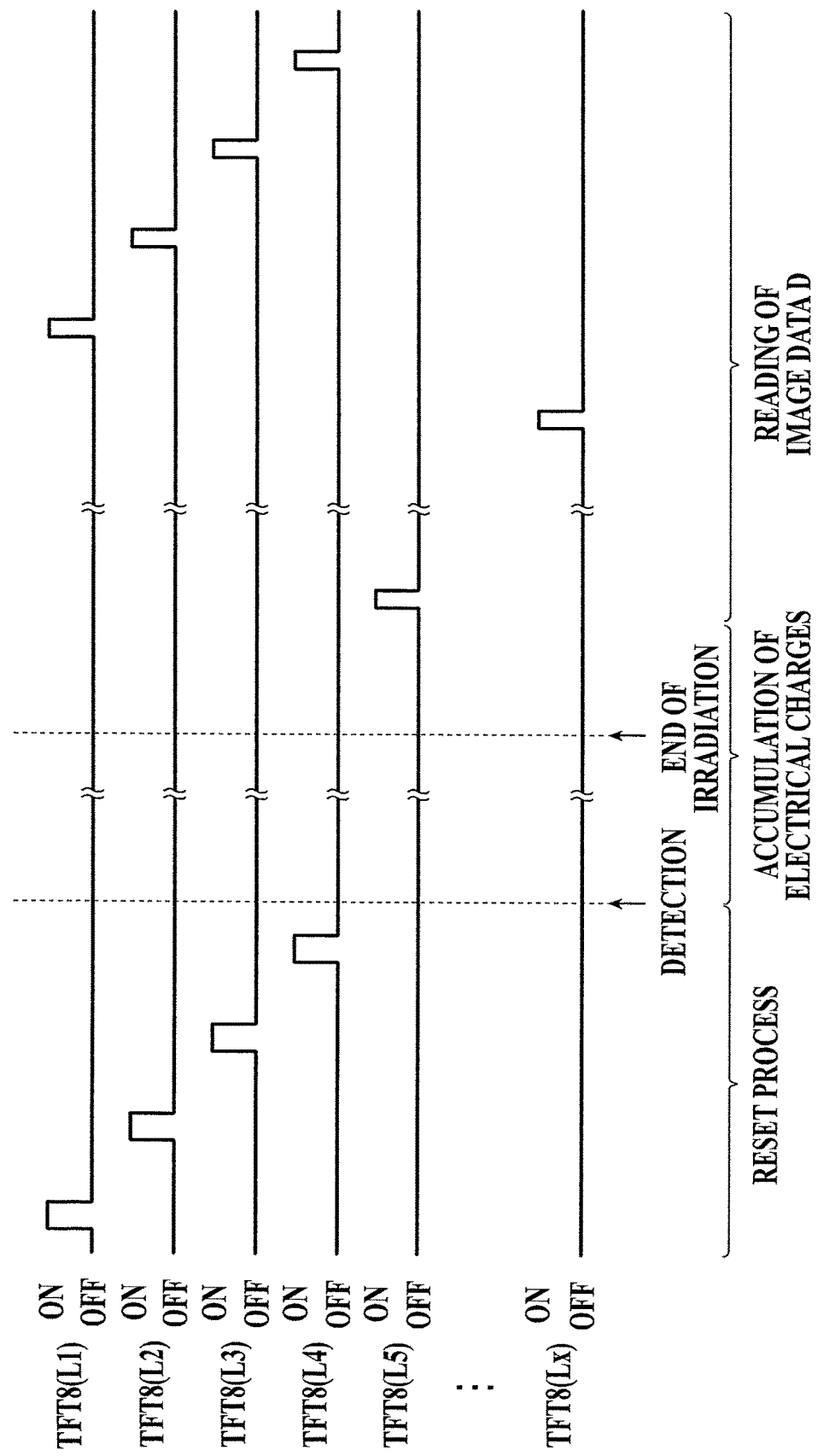
FIG. 4 is a timing chart illustrating the timing of applying an ON voltage to scanning lines during still image radiography performed by the radiographic image capturing device after detection of the start of irradiation of radiation.

For example, in a case of detection of the start of the irradiation of radiation by the control unit 22 on the basis of the output values from the X-ray sensor, the control unit 22 resets the radiation detectors 7 before the start of the irradiation of radiation, as illustrated in FIG. 4. The detection of the start of the irradiation of radiation on the basis of the output values from the X-ray sensor allows the control unit 22 to stop the reset process of the radiation detectors 7 for accumulation of electrical charges.

At a predetermined time after the accumulation of electrical charges, an ON voltage is sequentially applied from the gate driver 15b to the line L1 to Lx of the scanning lines 5, to read the image data D, as described above. In such a case, also, the offset data O is usually read before or after image capturing.

[Moving Image Mode]

In the moving image mode, the control unit 22 of the radiographic image capturing device 1 reads the image data D in accordance with the status of the moving image radiography (kymographic or tomosynthetic radiography, pulsed or continuous irradiation of radiation, time or frequency of irradiation, and intervals between irradiation operations).

Figure 5:
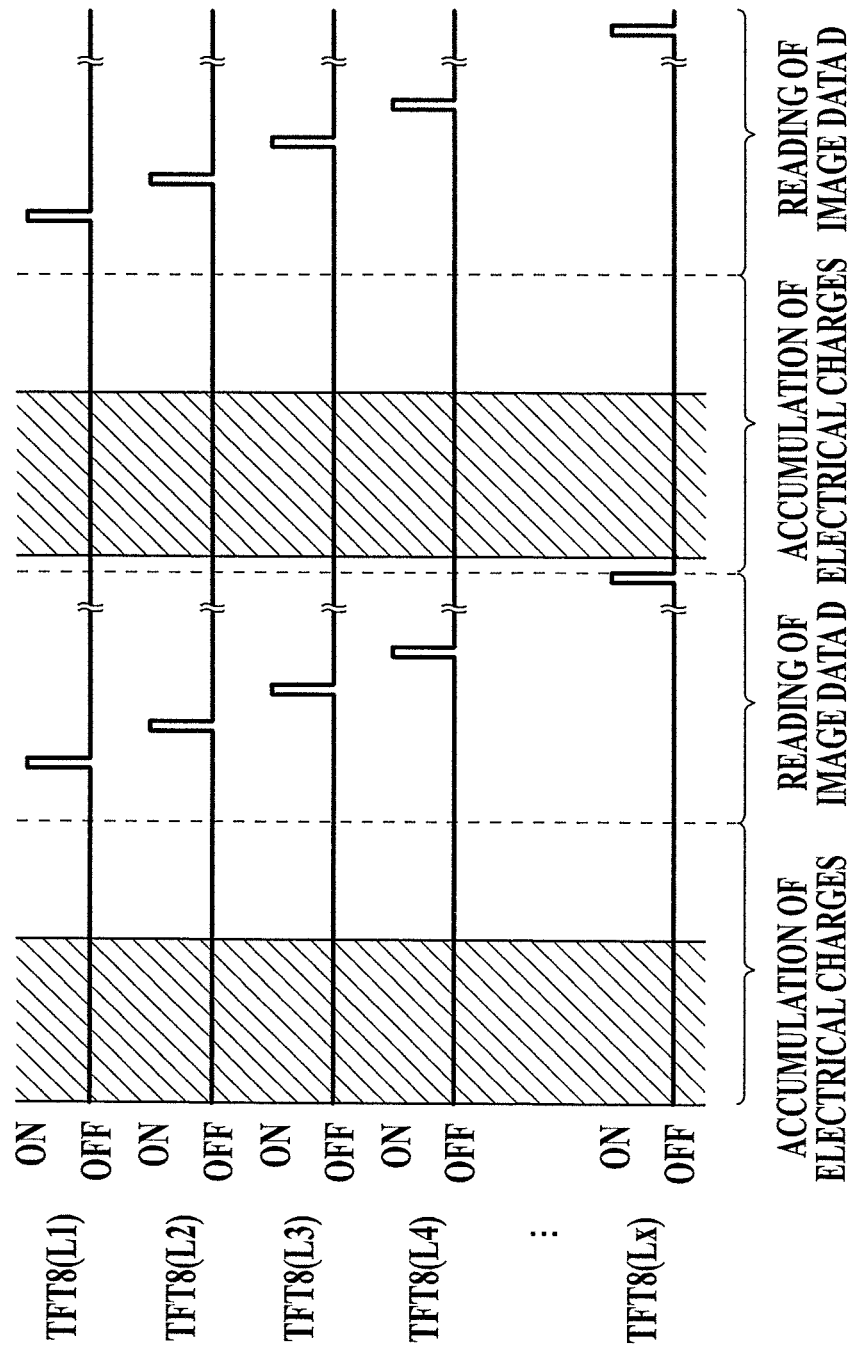
FIG. 5 is a timing chart illustrating the timing of applying an ON voltage to scanning lines when pulsed radiation is emitted for moving image radiography.

When pulsed radiation is emitted from the irradiator, for example, the radiographic image capturing device 1 is synchronized with the irradiator. With reference to FIG. 5, for example, the control unit 22 of the radiographic image capturing device 1 is synchronized with the irradiation timing of the radiation from the irradiator and reads the image data D during the time between two consecutive irradiation operations (see the hatched areas in the drawing). Specifically, the image data D is read for each frame.

In the moving image mode, unlike the still image mode, individual frames are sequentially captured usually without reading of the offset data O. If the time interval between consecutive irradiation operations is long, the offset data O may be read for each frame.

In the moving image mode, offset data O is usually not read during the time between two consecutive irradiation operations, and individual frames are sequentially captured, unlike in the still image mode. When the time interval between the two consecutive irradiation operations is long, the offset data O may be read for each frame. The offset data O corresponding to a single frame or multiple frames may be read before or after irradiation of pulsed or continuous irradiation of low-dose radiation.

The read image data D may be transferred to an external image processor after each radiographic operation (i.e., for each frame). Alternatively, the image data D may be stored in the storage unit 23 of the radiographic image capturing device 1 (see FIG. 2) and collectively transferred to the image processor. Such procedures are similar to those in the still image mode.

[Continuous Radiographic Mode]

The control unit 22 of the radiographic image capturing device 1 according to this embodiment has a continuous radiographic mode for reading the image data D without distinguishing between still image radiography and moving image radiography. In the still image mode and the moving image mode, the control unit 22 should read the image data D while in synchronization with the irradiator, as described above.

Figure 6:
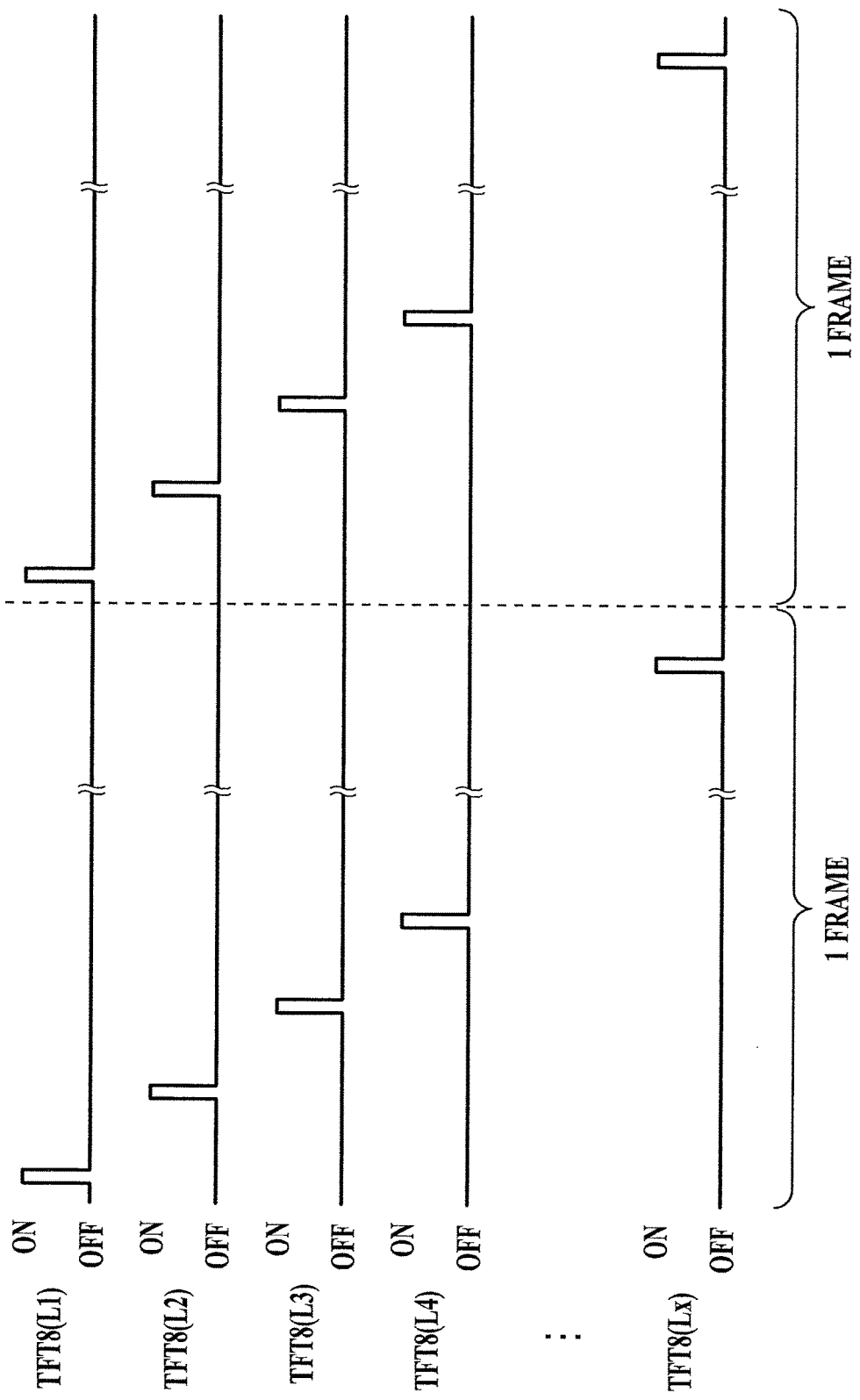
FIG. 6 is a timing chart illustrating the timing of applying an ON voltage to scanning lines during sequential reading of image data of individual frames in a continuous radiographic mode.

In the continuous radiographic mode, the control unit 22 sequentially reads the image data D of individual frames, as illustrated in FIG. 6, for example, without distinguishing between still image radiography and moving image radiography and without synchronization with the irradiator. A "frame (or single frame)" refers to the term during which an ON voltage is sequentially applied to the first line L1 to the last line Lx of the scanning lines 5 from the gate driver 15b of the scan driver 15 (see FIG. 2).

When radiography is to be started shortly after selection of the continuous radiographic mode for the radiographic image capturing device 1, the control unit 22 can start the reading of the image data D of the individual frames upon selection of the continuous radiographic mode, as described above.

In some cases, the reading of the image data D at the reader circuits 17 (see FIG. 2) requires a relatively large amount of electrical power. Thus, in a case where the time interval between the selection of the continuous radiographic mode and the actual start of the radiography is long, the consumption of the internal power source 24 (see FIG. 2) can be avoided through the following procedure, which is similar to that carried out when the radiographic image capturing device 1 is not in cooperation with the irradiator; the control unit 22 selects the continuous radiographic mode, instructs the start of detection of the irradiation with radiation of the radiographic image capturing device 1 with an X-ray sensor, for example, and sequentially reads the image data D of the individual frames upon detection of the start of the irradiation of radiation.

The radiographic image capturing device 1 may be configured such that the operator or radiologist can select one of the following processes to be carried out upon selection of the continuous radiographic mode: immediately starting the reading of the image data D of individual frames; or starting the detection of the irradiation of radiation upon selection of the continuous radiographic mode and reading the image data D of individual frames upon detection of the start of the irradiation.

[Configuration Inherent in Present Invention]

In this embodiment, when the operator (user) or radiologist operates the selection switch 26 of the radiographic image capturing device 1 (see FIG. 1) or operates an external controller or console to send a signal from the external controller to the radiographic image capturing device 1, to instruct still image radiography or moving image radiography to the radiographic image capturing device 1, the control unit 22 of the radiographic image capturing device 1 selects a radiographic mode of the radiographic image capturing device 1 corresponding to the instruction (i.e., the still image mode for still image radiography or the moving image mode for moving image radiography).

The control unit 22 carries out a radiographic process corresponding to the selected radiographic mode, as described above, and reads the image data D of a single radiographic image for the still image radiography or the image data D of multiple radiographic image in the moving image radiography.

In the case where an instruction for still image radiography or moving image radiography is not sent from the operator or radiologist or from an external controller or console, or in the case where the instruction is unknown due to communication failure with the external controller, the radiographic image capturing device 1 enters the continuous radiographic mode and sequentially reads the image data D of individual frames.

In other words, the control unit 22 of the radiographic image capturing device 1 cannot determine whether still image radiography or moving image radiography is to be performed, unless the operator (user) or radiologist selects the still image mode or the moving image mode of the radiographic image capturing device 1 directly or indirectly via the console.

In such a case, the control unit 22 according to this embodiment selects the continuous radiographic mode as the radiographic mode of the radiographic image capturing device 1, instead of the still image mode or the moving image mode. This allows the sequential reading of the image data D of individual frames for either still image radiography or moving image radiography, as described above.

The control unit 22 of the radiographic image capturing device 1 according to this embodiment monitors the communication status of the communication unit 30 (see FIG. 2) at predetermined timings. In a case where the wireless communication with the console fails due to an insufficient communication environment with weak signals and thus the radiographic mode is unknown even though the still image radiography and the moving image radiography are both available, the control unit 22 of the radiographic image capturing device 1 selects the continuous radiographic mode over the still image mode and the moving image mode.

[Selection of Continuous Radiographic Mode at Startup]

When the radiographic image capturing device 1 starts in response to an operation of the power switch 25 of the radiographic image capturing device 1 (see FIG. 1) by the operator or radiologist or the transmission of a wakeup signal from the console to the radiographic image capturing device 1, image capturing may begin without specifying still image radiography or moving image radiography.

Thus, the control unit 22 of the radiographic image capturing device 1 according to this embodiment enters the continuous radiographic mode immediately after startup. After startup of the radiographic image capturing device 1 as described above, the control unit 22 instructs the functional units of the radiographic image capturing device 1 to carry out specific initial operations. Then, the control unit 22 starts the reading of the image data D of individual frames or starts the detection of the irradiation of radiation (and then reads the image data D of individual frames immediately after detection of the irradiation).

[Operation]

The operation of the radiographic image capturing device 1 according to this embodiment will now be described.

The radiographic image capturing device 1 according to this embodiment is intended for use in a situation where a portable radiographic image capturing device 1 and a portable irradiator are used for radiography in the home of a patient or at a disaster site, as described above, i.e., radiography is performed independent from the control of an external controller or console, or a situation where communication between the radiographic image capturing device 1 and the console fails due to an insufficient communication environment with weak signals while the console and the irradiator are carried into a hospital room or the home of a patient on a visiting car.

The present invention can be applied to a radiographic image capturing device 1 that may experience communication failure with a console due to weak signals even in a radiographic room in a sufficient wireless environment. The present invention can also be applied to any type of situation involving lack of instruction on the radiographic mode (still image mode or moving image mode) of the radiographic image capturing device 1 or an unknown radiographic mode due to communication failure with an external controller or console.

The control unit 22 of the radiographic image capturing device 1 selects the still image mode or the moving image mode for the radiographic image capturing device 1 in response to an instruction on the still image radiography or the moving image radiography from the operator or radiologist, as described above. The control unit 22 selects the continuous radiographic mode if the radiographic mode (still image mode or moving image mode) is not instructed or if the radiographic mode is unknown due to communication failure with the external controller or console.

In the continuous radiographic mode, the control unit 22 controls the gate driver 15b of the scan driver 15, the reader circuits 17, and the other components (see FIG. 2) to sequentially read the image data D of individual frames, as illustrated in FIG. 6. The process of sequentially reading the image data D of individual frames when the continuous radiographic mode is selected will now be described. Alternatively, as described above, the detection of irradiation of radiation may be started when the continuous radiographic mode is selected, and the image data D of individual frames may be sequentially read when the irradiation of radiation is detected.

Figure 7:
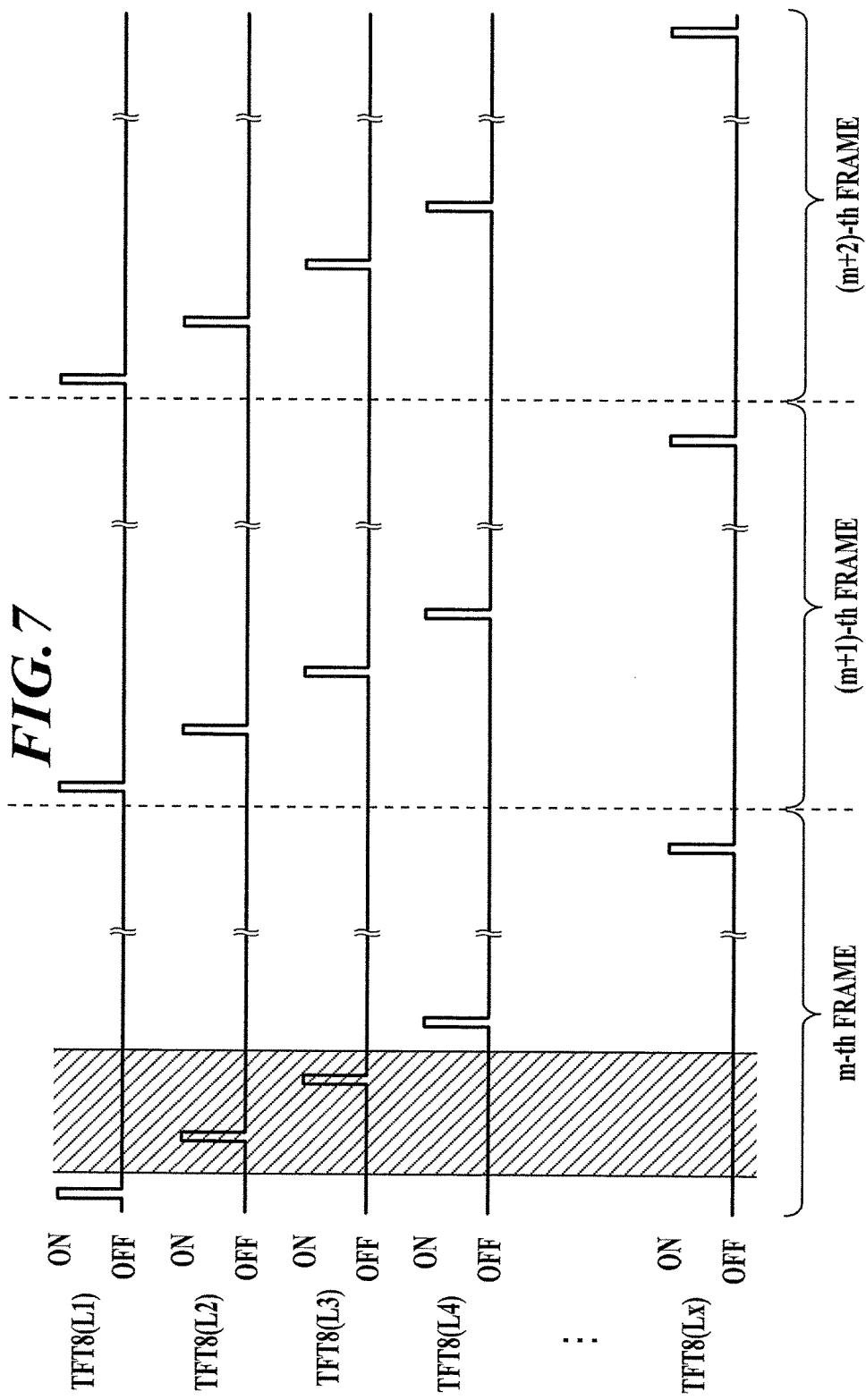
FIG. 7 is a timing chart illustrating an example timing of irradiation of the radiographic image capturing device with radiation in the continuous radiographic mode.
Figure 8:
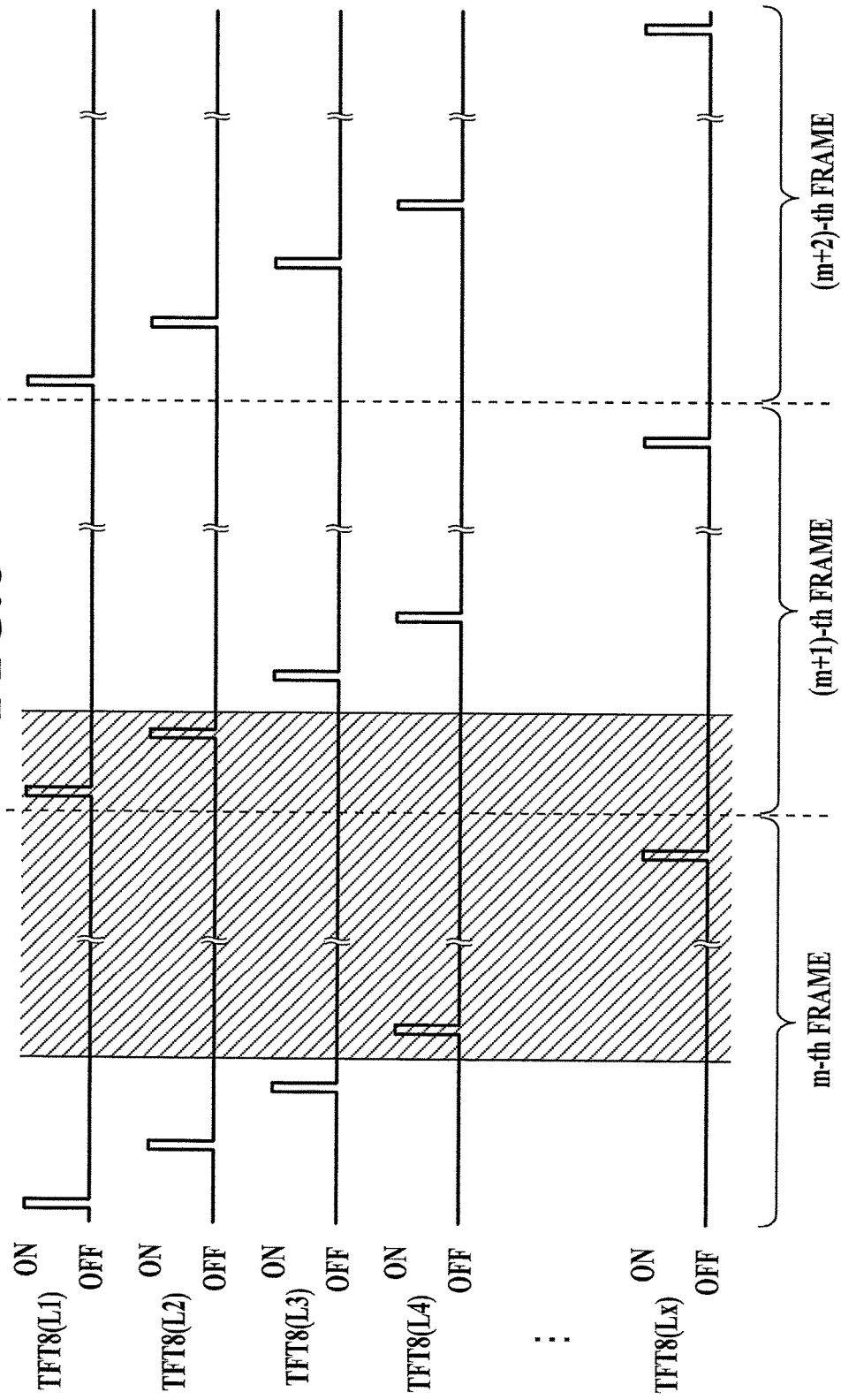
FIG. 8 is a timing chart illustrating another example timing of irradiation of the radiographic image capturing device with radiation in the continuous radiographic mode.

Still image radiography performed in the continuous radiographic mode of the radiographic image capturing device 1 may cause irradiation of radiation starting and ending during the reading of the image data D of a single frame, as illustrated in FIG. 7, or may cause irradiation of radiation across several frames, as illustrated in FIG. 8, depending on the irradiation time of radiation or frame rate (the time required for reading the image data D of a single frame).

In FIG. 8, the irradiation of radiation continues for two frames. Alternatively, the irradiation of radiation may continue for three frames or more. The hatched areas in FIGS. 7 and 8 and other drawings represent the irradiation time of radiation.

In the continuous radiographic mode, the radiographic image capturing device 1 sequentially reads the image data D while the radiographic image capturing device 1 is irradiated with radiation with the subject (not shown) disposed in front of the radiographic image capturing device 1, in both cases illustrated in FIGS. 7 and 8. Thus, the image data D, which contains components originating from the electrical charges generated in the radiation detectors 7 in response to the irradiation of radiation, can be read with precision and certainty.

An example of moving image radiography performed by the radiographic image capturing device 1 in the continuous radiographic mode includes kymographic radiography in which the radiographic image capturing device 1 is irradiated with pulsed radiation from the irradiator or is continuously irradiated with low-dose radiation, as described above. When the radiographic image capturing device 1 is irradiated with pulsed radiation, the irradiation of radiation and the reading of the image data D of individual frames establish the relationship illustrated in FIGS. 7 and 8. Thus, each time pulsed radiation is emitted, the image data D, which contains components originating from the electrical charges generated in the radiation detectors 7 in response to the irradiation of radiation, can be read with precision and certainty.

A small frame rate (i.e., substantial time required for the reading of the image data D of a single frame) causes double-exposure (multi-exposure) in the radiographic image capturing device 1 irradiated with a pulse of radiation emitted before the reading of the image data D corresponding to electrical charges generated in the radiation detectors 7 in response to the previously emitted pulse.

Thus, in the continuous radiographic mode of the radiographic image capturing device 1, it is preferred to set the maximum frame rate for the radiographic image capturing device 1 to read the image data D of individual frames.

When the radiographic image capturing device 1 in the continuous radiographic mode performs moving image radiography while being continuously irradiated with low-dose radiation, for example, the low-dose radiation is continuously emitted for a long time period in the range of several seconds to several tens of seconds once the irradiation of radiation starts.

Figure 9:
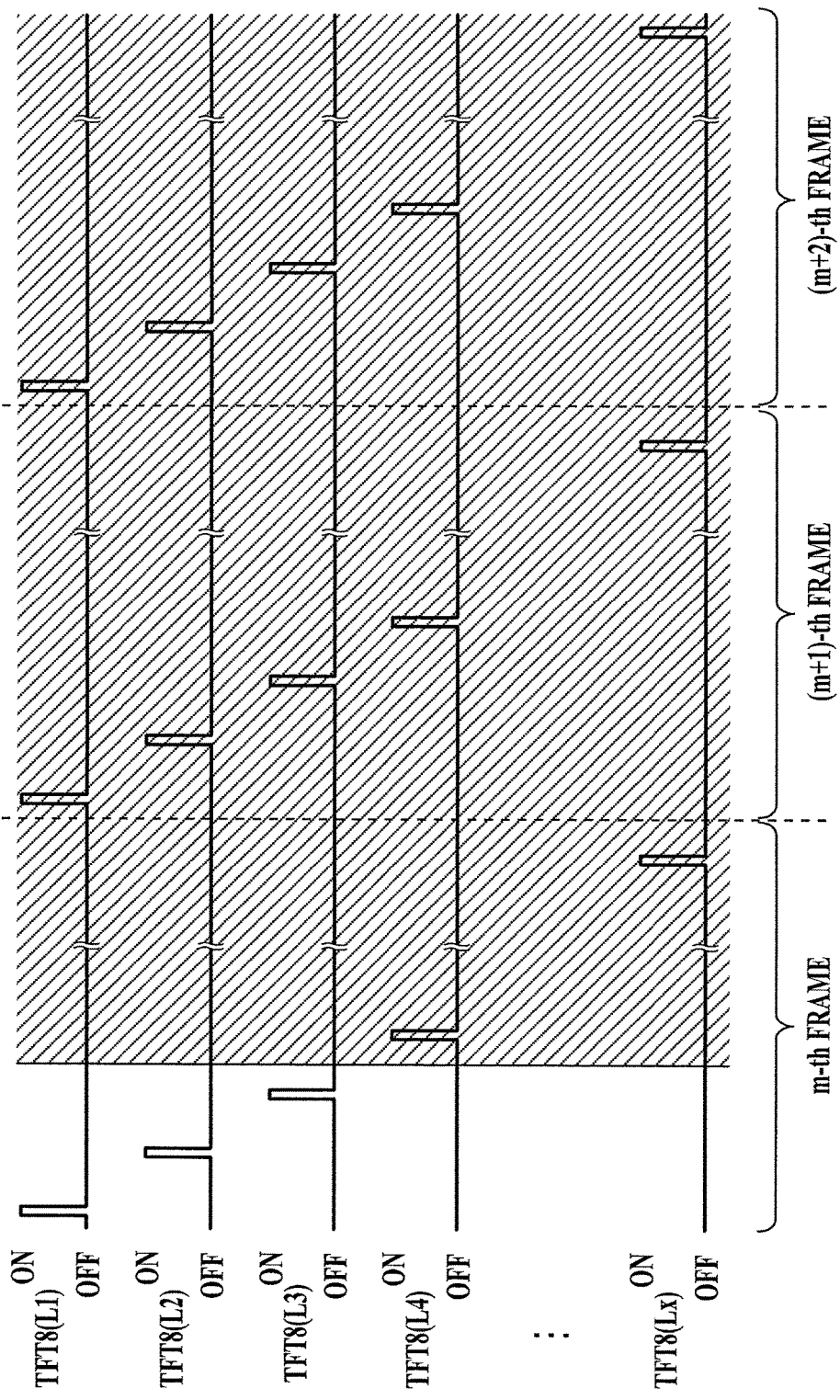
FIG. 9 is a timing chart illustrating an example timing of irradiation of the radiographic image capturing device with radiation during continuous radiation emission in moving image radiography.

In this embodiment, even in such a case, individual frames are sequentially read during the irradiation of radiation, as illustrated in FIG. 9. Thus, the image data D, which contains components originating from the electrical charges generated in the radiation detectors 7 in response to the irradiation of radiation, can be read with precision and certainty.

Advantageous Effects

As described above, the control unit 22 of the radiographic image capturing device 1 according to this embodiment can select the continuous radiographic mode to sequentially read the image data D of individual frames, even without instructions on still image radiography or moving image radiography from an external controller (or console) or the user (or radiologist), or even when the radiographic mode, i.e., still image mode or moving image mode, is unknown due to communication failure with the external controller.

Thus, either still image radiography or moving image radiography can be performed even without instructions on the type of radiography from the external controller (or console) or the user (or radiologist), or even when the radiographic mode, i.e., still image mode or moving image mode, is unknown due to communication failure with the external controller.

The image data D of individual frames can be sequentially read with precision in the still image radiography and moving image radiography performed under the situations described above, and both still image radiography and moving image radiography can be performed with precision in the continuous radiographic mode.

The switching of the radiographic mode of the radiographic image capturing device 1 to the continuous radiographic mode by the control unit 22 of the radiographic image capturing device 1 allows still image radiography and moving image radiography to be appropriately performed without switching between the still image mode and the moving image mode by the operator or radiologist. Thus, the operator can freely perform radiography without the troublesome operation of switching the radiographic mode.

[Announcement of Continuous Radiographic Mode]

Either the still image radiography or the moving image radiography can be performed in the continuous radiographic mode of the radiographic image capturing device 1. The still image mode, which is suitable for still image radiography (see FIGS. 3 and 4), is often preferred for capturing radiographic still images with precision, rather than performing still image radiography in the continuous radiographic mode.

Similarly, the moving image mode, which is suitable for moving image radiography (see FIG. 5), is often preferred for capturing multiple radiographic images with precision, rather than performing moving image radiography in the continuous radiographic mode. Radiographic still images captured by still image radiography in the still image mode and radiographic moving images captured by moving image radiography in the moving image mode can be readily generated without the identification process described later, which is required for images captured in the continuous radiographic mode.

When the radiographic mode of the radiographic image capturing device 1 is the continuous radiographic mode, it is preferred that the continuous radiographic mode is announced to the operator or radiologist so that the operator can determine to stay in the continuous radiographic mode or to switch to the still image mode or moving image mode.

Such an announcement to the operator or radiologist may be provided by illuminating the indicator 28 of the radiographic image capturing device 1 (see FIG. 1) in a predetermined color or a predetermined flashing pattern or by generating a beep. In the case where the operator has access to a smart phone or a portable information terminal, the announcement may be transmitted to the smart phone or the portable information terminal such that the announcement is displayed on the screen or a specific sound is generated.

[Transferring and Storing of Image Data D]

In the continuous radiographic mode, the image data D of the individual frames can be sequentially read and transferred to an external unit. Although not illustrated, the radiographic image capturing device 1 may be connected to a network, such as the Internet, via a wireless LAN, for example, and each time the image data D of a frame is read by the radiographic image capturing device 1, as described above, the image data D may be transferred to an external unit, such as a cloud server or a system connected to the network, and stored in the external unit.

The image data D of the individual frames read in the continuous radiographic mode may be stored in the storage unit 23 of the radiographic image capturing device 1 (see FIG. 2). In either case, the identification process, which is described later, can be certainly carried out on the image data D of the individual frames stored in the external unit, such as a cloud server, or the storage unit 23 of the radiographic image capturing device 1.

The entire image data D of the individual frames may be transferred and stored. Alternatively, the image data D of only frames containing the components originating from the electrical charges generated in the radiation detectors 7 in response to the irradiation of radiation may be transferred and stored.

Dark charges (also referred to as dark current) are constantly generated in the radiation detectors 7 due to the heat (temperature) generated by the radiation detectors 7. For example, the image data D of the frame captured before irradiation of radiation contains the dark charges discharged from the radiation detectors 7. This image data D has a value significantly smaller than that of the image data D read during the irradiation of radiation, which contains the components originating from the electrical charges generated in the radiation detectors 7 in response to the irradiation of radiation.

Thus, a threshold may be selected that can appropriately distinguish between the image data D originating from the dark charges and the image data D containing the components originating from the electrical charges generated in the radiation detectors 7 in response to the irradiation of radiation. In this way, the control unit 22 of the radiographic image capturing device 1, for example, can monitor the values of the image data D from the radiation detectors 7; and the image data D of frames having values smaller than the threshold may be discarded without transferring or storing, whereas the image data D of frames having values larger than or equal to the threshold may be transferred and stored.

This allows useless image data D that only contains data originating from dark charges to be discarded and useful image data D that contains the components originating from the electrical charges generated in the radiation detectors 7 in response to the irradiation of radiation to be transferred and stored. Thus, the data volume can be decreased for the image data D transferred from the radiographic image capturing device 1 to external units and the image data D stored in the storage unit 23 of the radiographic image capturing device 1.

In some cases in determining whether the values of the image data items D are larger than or equal to a threshold, noise may cause the image data items D originating from dark charges to appear as having values larger than or equal to the threshold. In such a case, the average value of a line L of the scanning lines 5 in each image data item D read by applying an ON voltage to the line L, as illustrated in FIG. 6, is calculated. If the average is larger than or equal to the threshold, the image data item D is determined to contain components originating from the electrical charges generated in the radiation detectors 7 in response to the irradiation of radiation.

Kymographic radiography, which is a form of moving image radiography, may be performed during constant emission of low-dose radiation from the irradiator, for example, as described above (see FIG. 9). In such a case, the values of image data items D of individual frames read after the start of irradiation of radiation are all larger than or equal to the threshold. Thus, in this case, the image data items D of all frames captured after the start of the irradiation of radiation are transferred and stored.

[Stopping of Reading of Image Data of Individual Frames]

The reading of the image data D at the reader circuits 17 (see FIG. 2) consumes a relatively large amount of electrical power, as described above. In such a case, if the reading of the image data D of individual frames (see FIG. 6) is continued for a long time after setting the radiographic image capturing device 1 to the continuous radiographic mode, the internal power source 24 of the radiographic image capturing device 1 may be completely consumed.

The control unit 22 of the radiographic image capturing device 1 may monitor the values of the image data D of the individual frames sequentially read as described above, and stop the reading of the image data D of the individual frames when the values of the image data D continue to indicate that the image data D originates from dark charges (i.e., the values of the image data D continue to be smaller than the threshold) for a predetermined time period (several seconds to several tens of seconds).

In this case, after stopping the reading of the image data D of individual frames, the control unit 22 of the radiographic image capturing device 1 remains in the continuous radiographic mode and may prepare for detection of the irradiation of radiation (for example, the radiation detectors 7 are reset for detection based on output values of an X-ray sensor).

The irradiation time in moving image radiography is at most several seconds to several tens of seconds. For example, if the image data D of individual frames is to be sequentially read after detection of the irradiation of radiation through the detection process started upon selection of the continuous radiographic mode, the reading of the image data D of the individual frames can be stopped after a predetermined time (within the range of several tens of seconds to approximately one minute) from the start of the reading of the image data D of individual frames.

This configuration certainly prevents the consumption of the internal power source 24 of the radiographic image capturing device 1 due to the unnecessary continuous reading of the image data D of individual frames.

If the start of the irradiation of radiation is detected through the detection process carried out after stopping the reading of the image data D of individual frames, the sequential reading of the image data D of individual frames is resumed.

[Identification of Image Data Captured by Still Image Radiography and Moving Image Radiography]

The process of identifying the image data D of individual frames captured by the radiographic image capturing device 1 in the continuous radiographic mode, as described above, as image data D captured by still image radiography or moving image radiography will now be described. The operation of a radiographic image capturing system 50 according to this embodiment (see FIG. 10) will also be described.

The identification process described below is carried out by an image processor 51 or a console. Alternatively, the control unit 22 of the radiographic image capturing device 1, for example, may carry out the identification process on the basis of image data D stored in the storage unit 23 or a cloud server. The identification process may be carried out after the series of radiographic operations is performed by the radiographic image capturing device 1 or may be carried out simultaneously with a radiographic operation by the radiographic image capturing device 1.

The image processor 51 according to this embodiment includes a general-purpose computer (not shown) including a CPU, a ROM, a RAM, an input/output interface, and other components mutually connected via a bus. Various programs, including a system program and processing programs, stored in the ROM are loaded into the RAM and executed to carry out various processes. Alternatively, the image processor 51 may be provided as a dedicated unit. The image processor 51 according to this embodiment is in the form of a console. Alternatively, the image processor 51 may be provided as a unit independent from the console.

The image processor 51 receives the image data D of individual frames (the image data D of only frames containing the components originating from the electrical charges generated in the radiation detectors 7 in response to the irradiation of radiation, as described above) read by the radiographic image capturing device 1 in the continuous radiographic mode from an external unit, such as a cloud server, or receives the image data D from the storage unit 23 of the radiographic image capturing device 1 via wired or wireless communication, as illustrated in FIG. 10.

The image processor 51 carries out the identification process as described below.

[Determination of Irradiation Time]

In the identification process, the image processor 51 determines the irradiation time during which the radiographic image capturing device 1 in the continuous radiographic mode is irradiated with radiation, on the basis of the image data D of individual frames sequentially read. This process will now be described in detail.

FIG. 11 is a schematic view illustrating the useful components of the image data D (the hatched area in the drawing), which originate from the electrical charges generated in the radiation detectors 7 in response to the irradiation of radiation (i.e., components of image data D having values larger than or equal to the threshold described above), when the radiographic image capturing device 1 in the continuous radiographic mode is irradiated with radiation as illustrated in FIG. 7, for example.

With reference to FIG. 7, an ON voltage is applied to the line L1 of the scanning lines 5 and then the reading of the image data D of the m-th frame starts before the irradiation of radiation. Thus, with reference to FIG. 11, the radiation detector 7 connected to the line L1 of the scanning lines 5 only reads useless image data D originating from dark charges (i.e., image data D having a value smaller than the threshold).

With reference to FIG. 7, an ON voltage is applied to the line L2 of the scanning lines 5 after the beginning of the irradiation of radiation. Thus, with reference to FIG. 11, useful image data D containing the components originating from the electrical charges generated in the radiation detectors 7 in response to the irradiation of radiation (i.e., the image data D having values larger than or equal to the threshold described above) is read from the radiation detectors 7 connected to the line L2 of the scanning lines 5. The image data D read from the line L3 of the scanning lines 5 is also similar to that read from the line L2.

With reference to FIG. 7, an ON voltage is applied to the lines L4 to Lx of the scanning lines 5 after the irradiation of radiation. Thus, with reference to FIG. 11, the image data D read from the radiation detectors 7 connected to the lines L4 to Lx of the scanning lines 5 also contain useful components originating from the electrical charges generated in the radiation detectors 7 in response to the irradiation of radiation.

Subsequently, useful components of the image data D of the (m+1)-th frame are read from the radiation detectors 7 connected to the line L1 of the scanning lines 5, as illustrated in FIG. 7, because image data D containing useful components originating from the electrical charges generated in the radiation detectors 7 in response to the irradiation of radiation are not read in the m-th frame.

With reference to FIG. 7, the lines L2 and L3 of the scanning lines 5 are irradiated with radiation even after applying the ON voltage ends in the m-th frame. Thus, the image data containing useful components originating from the electrical charges generated in the radiation detectors 7 in response to the irradiation of radiation after the application of the ON voltage in the m-th frame ends is read in the (m+1)-th frame. Thus, with reference to FIG. 11, the image data D read from the radiation detectors 7 connected to the lines L2 and L3 of the scanning lines 5 in the (m+1)-th frame is also useful image data D.

With reference to FIG. 7, since useful components of the image data D are read from the lines L4 to Lx of the scanning lines 5 in the m-th frame, only the useless components of the image data D originating from dark charges (components of the image data D having values smaller than the threshold described above) are read in the (m+1)-th frame.

Analysis of the components of the image data D read as illustrated in FIG. 11 can conduct the following conclusions: (1) The irradiation of radiation starts upon the first reading of a useful component of the image data D (i.e., a component of image data D having a value larger than or equal to the threshold), the first reading corresponding to the application of an ON voltage to the line L2 of the scanning lines 5 in the m-th frame in FIG. 7; and (2) The irradiation of radiation ends one frame before the last reading of a useful component of the image data D, the last reading corresponding to the application of an ON voltage to the line L3 of the scanning lines 5 in the (m+1)-th frame or, in other words, the irradiation ends when an ON voltage is applied to the line L3 of the scanning lines 5 in the m-th frame.

Figure 12:
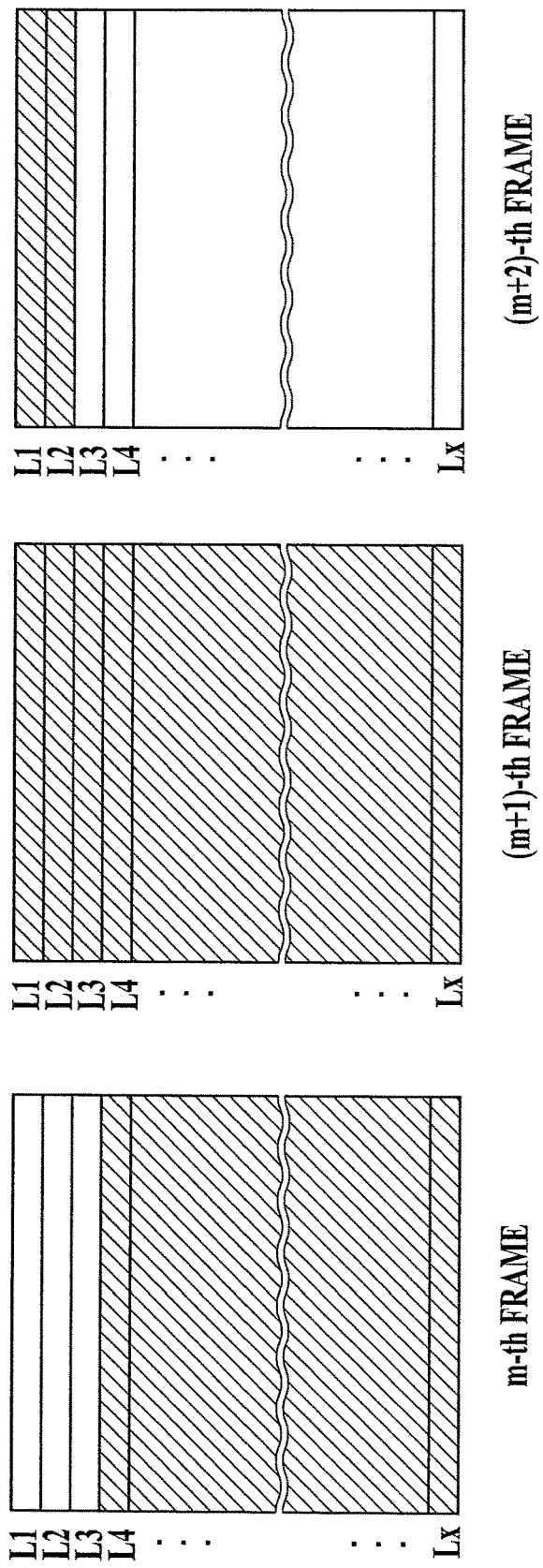
FIG. 12 schematically illustrates the range of useful image data read when radiation is emitted in the timing illustrated in FIG. 8 in a continuous radiographic mode.

With reference to FIG. 8, an ON voltage is applied to the line L4 and the subsequent lines L of the scanning lines 5 in the m-th frame after the start of the irradiation of radiation. Thus, as illustrated in FIG. 12, useful components of the image data D are read from the radiation detectors 7 connected to the line 4 and the subsequent lines of the scanning lines 5 in the m-th frame.

The image data containing useful components originating from the electrical charges generated in the radiation detectors 7 in response to the irradiation of radiation after the application of an ON voltage to the line L2 of the scanning lines 5 in the (m+1)-th frame is read in the (m+2)-th frame. The useful components of the image data D in this case are indicated by the hatched area in FIG. 12.

The analytical result described above can be applied to lead to the following conclusions:
(1) The irradiation of radiation starts upon the first reading of a useful component of the image data D (i.e., a component of image data D having a value larger than or equal to the threshold), i.e., when an ON voltage is applied to the line L4 of the scanning lines 5 in the m-th frame; and
(2) The irradiation of radiation ends one frame before the last reading of a useful component of the image data D, i.e., the last reading corresponding to the application of an ON voltage to the line L2 of the scanning lines 5 in the (m+2)-th frame or, in other words, the irradiation ends when an ON voltage is applied to the line L2 of the scanning lines 5 in the (m+1)-th frame. This analytical result coincides with the time period during which radiation is emitted in FIG. 8.

Thus, the image processor 51 according to this embodiment uses the analytical results (1) and (2) as criteria for the determination of the irradiation time T from the start to the end of the irradiation of the radiographic image capturing device 1 with radiation in the continuous radiographic mode, on the basis of the image data D of the sequentially read individual frames.

For example, with reference to FIG. 11, the irradiation time T from the start to end of the irradiation of the radiographic image capturing device 1 with radiation determined on the basis of the image data D of the sequentially read individual frames is the time from the application of an ON voltage to the line L2 of the scanning lines 5 in the m-th frame to the application of an ON voltage to the line L3 of the scanning lines 5 in the m-th frame. Thus, the irradiation time T is determined to be the time required for the reading of the image data D from the radiation detectors 7 connected to two scanning lines 5.

For example, with reference to FIG. 12, the irradiation time T from the start to end of the irradiation of the radiographic image capturing device 1 with radiation determined on the basis of the image data D of the sequentially read individual frames is the time from the application of an ON voltage to the line L4 of the scanning lines 5 in the m-th frame to the application of an ON voltage to the line L2 of the scanning lines 5 in the (m+1)-th frame. Thus, the irradiation time T is determined to be the time required for the reading of the image data D from the radiation detectors 7 connected to x−1 scanning lines 5.

In some cases, whether the image data D of individual frames captured by the radiographic image capturing device 1 in the continuous radiographic mode is captured by still image radiography or moving image radiography can be determined on the basis of the determined irradiation time T. The image processor 51 according to this embodiment determines whether the image data D of individual frames is captured by still image radiography or moving image radiography on the basis of the determined irradiation time T.

For example, if the irradiation time T determined as described above is 1 second or more, it can be determined that moving image radiography or kymographic radiography has been performed during continuous irradiation of radiation. In such a case, the image processor 51 determines that the image data D of individual frames captured by the radiographic image capturing device 1 in the continuous radiographic mode is captured by moving image radiography.

In some cases, the radiation emitted during the determined irradiation time T can be identified as radiation emitted for still image radiography or one of the pulses of radiation emitted for moving image radiography. In such a case, the image processor 51 determines whether the image data D of individual frames captured by the radiographic image capturing device 1 in the continuous radiographic mode is captured by still image radiography or moving image radiography, on the basis of the irradiation time T.

[Determination of Time Interval]

For example, the radiation incident on the radiographic image capturing device 1 can be determined to be radiation emitted for still image radiography or pulsed radiation emitted for moving image radiography through the determination of the time interval τ between the end of the irradiation of radiation and the start of the next irradiation of radiation.

That is, the start and end of the irradiation of radiation can be determined on the basis of the criteria (1) and (2) for the determination of the irradiation time T described above. The determination of the time from the end of the irradiation of radiation to start of the next irradiation of radiation can determine the time interval τ between the end of the irradiation of radiation and the start of the next irradiation of radiation.

Figure 13:
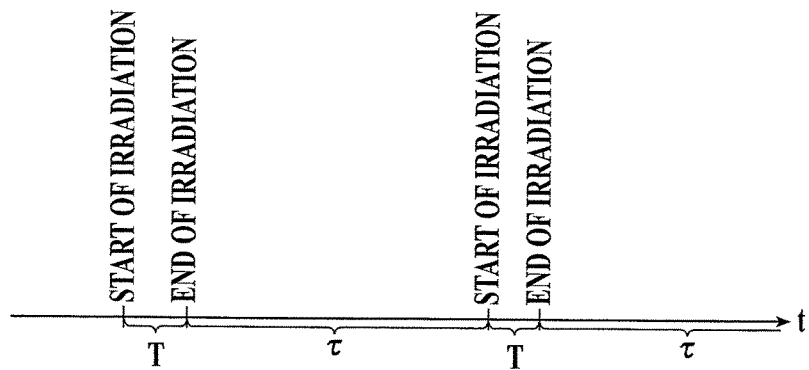
FIG. 13 illustrates the relationship between time intervals and irradiation time.

The relationship between the time interval τ and the irradiation time T described above is illustrated in FIG. 13. That is, the irradiation time T represents the time period during which radiation is emitted, and the time interval τ represents the time interval between the end of the irradiation of radiation and the start of the next irradiation of radiation. In still image radiography, the time interval τ between the end of the irradiation of radiation and the start of the next irradiation of radiation is at least several seconds, whereas, radiation in moving image radiography is usually emitted in pulses with small time intervals of several tens of milliseconds to several hundreds of milliseconds.

The image processor 51 according to this embodiment determines the image data D as image data captured by still image radiography if the time interval τ is 1 second or more and by moving image radiography if the time interval τ is less than the 1 second, for example.

Besides 1 second, the reference time for the determination may be any appropriate time, such as 2 seconds. In the case where the time interval τ between two image data items D is at least several seconds, the two image data items D are determined to be captured through two different radiographic operations by still image radiography and/or moving image radiography.

In the case of image data items D captured through two radiographic operations by only still image radiography or by still image radiography and moving image radiography, the image data items D can be clearly determined to be captured through two different radiographic operations. However, in the case of image data items D captured through two radiographic operations both by moving image radiography, from the view point of time-series, the image data items D are determined to be captured through two different radiographic operations by moving image radiography if the time interval τ between the moving images is at least several seconds.

[Determination of Dose Rate of Radiation]

In still image radiography, radiation is emitted once, whereas in moving image radiography, radiation is emitted several times. Thus, if the dose rate DR (i.e., dose per unit time) of the radiation emitted during moving image radiography is approximately the same as that in still image radiography, the subject or patient will be exposed to a significantly large total dose of radiation.

In some cases, a filter may be disposed in front of the irradiator to reduce the dose rate DR of the radiation emitted from the irradiator during moving image radiography. The use of such a filter usually significantly reduces the dose rate DR of the radiation emitted during moving image radiography compared to that emitted during still image radiography. A larger dose rate DR of the radiation incident on the radiographic image capturing device 1 results in a larger value of the image data D read from the radiation detectors 7.

The image processor 51 according to this embodiment calculates the dose rate DR of the radiation incident on the radiographic image capturing device 1 from the values of the image data items D of the individual frames and determines whether the image data items D are captured by still image radiography or moving image radiography on the basis of the calculated dose rate DR of the radiation (i.e., whether the calculated dose rate DR is larger than or equal to a threshold or smaller than a threshold).

In this case, the image processor 51 stores information on the conversion factor for the image data D and the dose rate DR of the incident radiation for each radiographic image capturing device 1 in a storage unit, for example. When determining the dose rate DR of the radiation on the basis of the individual image data items D, sometimes the values of the image data items D may appear larger than the actual values due to noise, and thus, the calculated dose rate DR of the radiation becomes larger than the actual dose rate DR.

Thus, the calculation of the dose rate DR of the radiation on the basis of the image data items D can be replaced with the calculation of the average of the values of the lines L of the scanning lines 5 corresponding to the useful components of the image data D originating from the electrical charges generated in the radiation detectors 7 in response to the irradiation of radiation (see the hatched area in FIGS. 11 and 12) and calculation of the dose rate DR of the radiation on the basis of the calculated average.

Instead of converting the image data D and the average value of the components of the image data D into the dose rate DR of radiation, the image data D may be determined to be captured by still image radiography or moving image radiography on the basis of the actual value of the image data D or the actual average value of the components of the image data D. In such a case, a threshold for determining whether the image data D is captured by still image radiography or moving image radiography is preliminarily determined for the value of the image data D or the average value of the components of the image data D. In this way, the image data D can be determined to be captured by still image radiography or moving image radiography on the basis of the value larger than or equal to the threshold or smaller than the threshold.

The image processor 51 determines whether the image data D is captured by still image radiography or moving image radiography through at least one of or all of the schemes described above involving the irradiation time T, the time interval T, the dose rate DR, and the actual value of the image data D (or the average value of the components). In this way, the image data D can be precisely determined to be captured by still image radiography or moving image radiography.

In the barium meal test described above, for example, moving image radiography is performed while continuously irradiating a subject with low-dose radiation, and still image radiography is performed at a specific timing during the moving image radiography by irradiating the subject with a relatively large dose of radiation. In such a case, moving image radiography is performed during the time period in the reading process of the image data D of individual frames between the application of an ON voltage to the first line L1 of the scanning lines 5 to a specific line L and reading of the image data D, and then still image radiography is performed by increasing the dose rate from the line next to line L in the scanning lines 5.

Thus, in this case, the image data D corresponding to a single frame contains components captured by both still image radiography and moving image radiography. Similarly, after ending the still image radiography and switching back to the moving image radiography by continuously irradiating the subject with low-dose radiation, the image data D corresponding to a single frame contains components captured by both still image radiography and moving image radiography.

Thus, the image data D corresponding to a single frame should be categorized into image data components captured by still image radiography and image data components captured by moving image radiography. This can be precisely done through determination of the image data components captured by still image radiography and moving image radiography on the basis of the dose rate of the radiation (or the value of the image data D or the average value of the components of the image data D), as described above.

[Addition of Information to Image Data]

The information on the results of the determination process carried out above, i.e., whether the image data D is captured by still image radiography or moving image radiography, is written to the image data D by the image processor 51 in the header of the image data D, for example.

Among the multiple image data items D captured by moving image radiography, the image data items D that are determined to be a series of image data captured in a single operation of moving image radiography on the basis of the time interval τ between the end of the irradiation of radiation and the start of the next irradiation of radiation, determined as described above, can be treated as a single group by adding information indicating that the image data items D are captured in a single operation of moving image radiography.

It is preferred that information on the order of capturing be added to the series of image data items D captured in a single operation of moving image radiography, such as numbers indicating the order of capturing (i.e., in chronological order).

For the identification process carried out at the radiographic image capturing device 1 as described above, the control unit 22 of the radiographic image capturing device 1 adds information to the image data D indicating whether the image data D is captured by still image radiography or moving image radiography and information indicating whether the image data items D captured by moving image radiography belong to a series of image data items captured in a single operation of moving image radiography, and transfers the image data D to a cloud server or the image processor 51.

Regardless of whether the identification process is to be carried out at the image processor 51 or the control unit 22 of the radiographic image capturing device 1, the addition of information indicating whether the image data D is captured by still image radiography or moving image radiography to the image data D certainly prevents the generation of a radiographic image through false recognition of a radiographic still image as a radiographic moving image or vice versa during the generation of a radiographic still image or a radiographic moving image, described below.

This allows accurate identification of the image data D captured by the radiographic image capturing device 1 as image data captured by still image radiography or moving image radiography and thus, appropriate generation of a radiographic still image or multiple radiographic moving images on the basis of the image data D.

[Generation of Radiographic Still Image and Radiographic Moving Image by Image Processor]

The image processor 51 generates a radiographic still image or multiple radiographic moving images on the basis of the information on the identification result added to the image data D.

The image processor 51 generates a radiographic still image on the basis of the image data D containing information indicating that the image data is captured through still image radiography and generates multiple radiographic moving images on the basis of the image data D containing the information indicating that the image data is captured through moving image radiography. Details will now be described.

Among the image data D captured through still image radiography and the image data D captured through moving image radiography, the image data D captured through moving image radiography through irradiation of pulsed radiation may be read across multiple frames in useful components originating from the electrical charges generated in the radiation detectors 7 in response to the irradiation of radiation, as illustrated in FIGS. 7, 8, 11, and 12.

In the examples illustrated in FIGS. 7 and 11, the electrical charges generated in the radiation detectors 7 connected to the lines L2 and L3 of the scanning lines 5 are read to be the image data D in the m-th and (m+1)-th frames.

Thus, the actual image data D to be read from the radiation detectors 7 connected to the lines L2 and L3 of the scanning lines 5 should correspond to the sum of the image data D of the m-th frame and the image data D of the (m+1)-th frame. The image data D contains not only the electrical charges generated in the radiation detectors 7 in response to the irradiation of radiation but also an offset caused by dark charges.

If the image data D contains the sum of the components of the image data D from the lines L2 and L3 of the scanning lines 5 in the m-th and (m+1)-th frames, the component of the line L1 of the scanning lines 5 in the (m+1)-th frame and the components of the lines L4 to Lx of the scanning lines 5 in the m-th frame and the components from the radiation detectors 7 connected to the lines L2 and L3 of the scanning lines 5 will contain a cumulative offset of two frames caused by the dark charges, whereas the components from the radiation detectors 7 connected to the other lines L1 and L4 to Lx of the scanning lines 5 will contain an offset of only one frame caused by the dark charges. Thus, the generated radiographic image may have uneven contrast density.

With reference to FIGS. 7 and 11, in the case where the useful components of the image data D originating from the electrical charges generated in the radiation detectors 7 in response to the irradiation of radiation are read in two frames (m-th and (m+1)-th frames), the components of the image data D, as illustrated in FIG. 11, read from all of the radiation detectors 7 connected to the lines L1 to Lx of the scanning lines 5 in the m-th and (m+1)-th frames are added together (i.e., all of the hatched and non-hatched components in FIG. 11 are added together), to calculate the image data D.

This is also the same for the image data illustrated in FIGS. 8 and 12. In the case where the useful components of the image data D originating from the electrical charges generated in the radiation detectors 7 in response to the irradiation of radiation are read in three frames (m-th to (m+2)-th frames), the components of the image data D, as illustrated in FIG. 12, read from all of the radiation detectors 7 connected to the lines L1 to Lx of the scanning lines 5 in the m-th to (m+2)-th frames are added together (i.e., all of the hatched and non-hatched components in FIG. 12 are added together), to calculate the image data D.

Offset correction can be carried out on the useful components of the image data D originating from the electrical charges generated in the radiation detectors 7 in response to the irradiation, such as the components from the lines L4 to Lx of the scanning lines 5 in the m-th frame in FIG. 7, with offset data items O for the lines, the offset data items O being the components of the image data D from the lines in the latest frame that only provide useless components of the image data D originating from dark charges, such as the lines L4 to Lx of the scanning lines 5 in the (m+1)-th frame illustrated in FIG. 7. In the continuous radiographic mode, the useless components of the image data D originating from dark charges in the latest frame are assigned to be offset data items O. Thus, the offset data items O can be assigned in the most recent frame without accumulation of electrical charges, and correction can be performed with high precision.

The image data D obtained through the addition of the components of the image data D in the m-th and (m+1)-th frames, such as the components of the image data D from the lines L2 and L3 of the scanning lines 5 in FIG. 7, contains a cumulative offset of two frames originating from dark charges. Offset data O can be assigned to be the image data D corresponding to the lines in the latest frame that only provide useless components of the image data D originating from dark charges, such as the lines L2 and L3 of the scanning lines 5 in the (m+2)-th frame in FIG. 7. The offset data O can be used to carry out offset correction on the obtained image data D for a number of times equal to the number of added frames. Thus, the cumulative offset can be corrected with precision.

Offset correction on the lines of the image data D can be carried out for a number of times equal to the number of added frames to cancel out the cumulative offset originating from dark charges even when the added number of frames differ for the components of the image data D from the different lines; for example, the image data D corresponding to the lines L2 and L3 of the scanning lines 5 illustrated in FIG. 7 is obtained by adding the components in the m-th and (m+1)-th frames, whereas the image data D corresponding to the lines L4 to Lx of the scanning lines 5 is obtained from the m-th frame without addition. With this, unevenness in the radiographic image can be suppressed.

The components of the image data D from the lines that only provide useless image data D originating from dark charges in multiple frames among the frames to be corrected (e.g., the latest multiple frames) may be added together to obtain the offset data O.

The image processor 51 carries out known image processing, such as gain correction and gradation processing, on the image data D calculated as described above, and generates a radiographic still image on the basis of the image data D captured through still image radiography and multiple radiographic moving images on the basis of the image data D captured through moving image radiography.

Among the image data items D captured through moving image radiography, the image data item D captured through moving image radiography through continuous irradiation of low-dose radiation (see FIG. 9) contains useful components of the image data D originating from the electrical charge generated in the radiation detectors 7 in response to the irradiation of radiation in consecutive frames.

In such a case, a radiographic image can be generated for each frame. That is, a single radiographic image can be generated in every frame. In this case, the number of radiographic moving images generated is equal to the number of frames containing useful components of the image data D originating from the electrical charge generated in the radiation detectors 7 in response to the irradiation of radiation.

For example, among the consecutive frames containing useful components of the image data D originating from the electrical charge generated in the radiation detectors 7 in response to the irradiation of radiation, the image data D corresponding to a single frame is extracted at every predetermined number of frames among the consecutive frames. A radiographic image is generated on the basis of these extracted image data items D, to generate multiple radiographic moving images.

In the case where a single frame contains both the image data D captured through still image radiography and the image data D captured through moving image radiography as in the barium meal test described above, the image data D of the still image radiography and the image data D of the moving image radiography distinguished as described above are inevitably subjected to separate processes.

As described above, the image processor 51 generates a radiographic still image on the basis of the image data D containing information indicating that the image data is captured through still image radiography and multiple radiographic moving images on the basis of the image data D containing information indicating that the image data is captured through moving image radiography. In this way, a radiographic still image or multiple radiographic moving images can be appropriately generated on the basis of image data D that is precisely identified to be either image data D captured through still image radiography or moving image radiography.

[Identification with Radiography Order Information]

The radiographic image capturing device 1 according to this embodiment is not intended for radiography based on the radiography order information in a situation where the radiographic image capturing device 1 is used for radiography in the home of a patient or at a disaster site. The image processor 51, however, stores radiography order information for establishing correspondence between the generated radiographic images and the corresponding radiography order information items. The radiography order information assigns still image radiography (simple radiography or general radiography) or moving image radiography.

For example, during identification by the image processor 51, the image data items D of the frames captured by the radiographic image capturing device 1 in the continuous radiographic mode can be arranged in chronological order of capturing and connected to the radiography order information items arranged in the order of capturing, to identify whether the image data items D are captured through still image radiography or moving image radiography. That is, the image processor 51 can use the radiography order information for identification.

[Post-Classification of Still Images and Moving Images]

The embodiments above describe still image radiography or moving image radiography performed by the radiographic image capturing device 1 in the continuous radiographic mode in accordance with the intension of the operator or radiologist. Alternatively, the operator may generate still images and moving images from the image data items D of the captured frames after radiography is performed in the continuous radiographic mode without distinguishing between still images and moving images.

In such a case, the control unit 22 of the radiographic image capturing device 1 selects the continuous radiographic mode, sequentially reads the image data D of individual frames, as illustrated in FIG. 6, and stores the image data D of the individual frames in the storage unit 23 (see FIG. 2).

After the radiography, the operator or radiologist can directly operate the radiographic image capturing device 1 or operate a smart phone or portable information terminal to input an instruction for the preparation of image data D of moving image radiography on the basis of the image data D of the individual frames. In such a case, the control unit 22 of the radiographic image capturing device 1 reads the image data D of the individual frames from the storage unit 23 and prepares the image data D of moving image radiography on the basis of the image data D of the individual frames.

That is, as described above, upon reception of an instruction from the operator or radiologist for the preparation of the image data D of moving image radiography after the radiography during continuous irradiation of low-dose radiation (see FIG. 9), the control unit 22 of the radiographic image capturing device 1 prepares the image data D of still image radiography corresponding to a single frame or prepares image data D of multiple frames of moving image radiography on the basis of the image data D corresponding to frames extracted at every predetermined number of frames among the consecutive frames.

In response to an instruction from the operator or radiologist for the preparation of image data D of still image radiography, the control unit 22 of the radiographic image capturing device 1 transmits the image data D corresponding to single frames extracted at every predetermined number of frames among the consecutive frames (or the image data D for all frames), to display the extracted data (or the entire image data) on a display unit of the portable information terminal, for example.

The operator observes the displayed data and sends information, such as a frame number, for assigning the frame of the still image to be prepared. The signal values of the pixels in the assigned frame can be increased to a certain level by adding the image data D corresponding to the pixels in a predetermined number of frames (e.g., two or three frames) including the assigned frame, to prepare the image data D of still image radiography corresponding to a single frame.

Upon reception of an instruction from the operator or radiologist for the preparation of the image data D of moving image radiography after radiography is performed during irradiation of pulsed radiation (see FIGS. 7 and 8), the control unit 22 of the radiographic image capturing device 1 prepares the image data D of moving image radiography corresponding to multiple frames through addition of the image data items D in the frames containing useful components of the image data D originating from the electrical charge generated in the radiation detectors 7 in response to the irradiation of radiation, as illustrated in FIGS. 11 and 12.

Upon reception of an instruction from the operator or radiologist for the preparation of the image data D of still image radiography, the control unit 22 of the radiographic image capturing device 1 can prepare the image data D of moving image radiography corresponding to several frames, in a manner similar to that described above, transmit the prepared image data D to a portable information terminal, display the image data D on a display unit for selection by the operator, and prepare the image data D of still image radiography corresponding to a single frame selected by the operator among the displayed image data D corresponding to multiple frames.

Alternatively, the control unit 22 can transmit the entire image data D for all frames (raw data) or extracted data corresponding to frames extracted at every predetermined number of frames among the consecutive frames (extracted raw data), such as the data before addition illustrated in FIGS. 11 and 12, to a portable information terminal, display the data on a display unit for selection by the operator, carry out the processing illustrated in FIGS. 11 and 12 on the frames including the frame corresponding to the frame number selected by the operator, add together the image data items D corresponding to the individual frames, and prepare the image data D of still image radiography corresponding to a single frame.

In the process described above, upon reception of the image data D of still image radiography corresponding to a single frame, which is prepared by and sent from the radiographic image capturing device 1, the image processor 51 prepares a radiographic still image as described above on the basis of this image data D. Alternatively, upon reception of the image data D of moving image radiography corresponding to multiple frames, which is prepared and sent from the radiographic image capturing device 1, the image processor 51 generates multiple radiographic moving images on the basis of this image data D.

In either of these cases, the operator or radiologist can perform radiography in the continuous radiographic mode without distinguishing between still images and moving images, and still images and moving images can then be generated on the basis of the captured image data D corresponding to the individual frames. Thus, the radiographic image capturing device 1 and the radiographic image capturing system 50 can perform radiography with high flexibility, which is convenient for the operator or radiologist.

Still images and moving images can be generated at the image processor 51 in accordance with an instruction from the operator or radiologist. In such a case, the image data D corresponding to the individual frames read in the continuous radiographic mode can be transferred from the radiographic image capturing device 1 to the image processor 51 via a cloud server or an external unit, or the image data D corresponding to the individual frames stored in the storage unit 23 of the radiographic image capturing device 1 is transferred from the radiographic image capturing device 1 to the image processor 51 after radiography.

Similar to the operation of the radiographic image capturing device 1 described above, the image processor 51 prepares the image data D of still image radiography corresponding to a single frame or the image data D of moving image radiography corresponding to multiple frames on the basis of the image data D corresponding to the individual frames read by the radiographic image capturing device 1 in the continuous radiographic mode, and prepares a radiographic still image on the basis of the prepared image data D of still image radiography corresponding to a single frame or multiple radiographic moving images on the basis of the prepared image data D of moving image radiography corresponding to multiple frames.

In this way, the operator or radiologist can perform radiography in the continuous radiographic mode without distinguishing between still images and moving images, and still images and moving images can then be generated on the basis of the captured image data D corresponding to the individual frames. Thus, the radiographic image capturing device 1 and the radiographic image capturing system 50 can perform radiography with high flexibility, which is convenient for the operator or radiologist.

[Transmission Failure of Image Data]

In this embodiment, if the type of radiography, i.e., still image radiography or moving image radiography, is unknown due to a communication failure with an external unit or console, the radiographic image capturing device 1 selects the continuous radiographic mode for radiography. In such a communication failure with an external unit, the radiographic image capturing device 1 may not be able to send the image data D of individual frames to a cloud server.

In such a case, the unsent image data D of individual frames can be temporarily stored in the storage unit 23 of the radiographic image capturing device 1 until the communication is reestablished, to resume the transmission of the image data D of individual frames. The transmission of the image data D of individual frames may be resumed from the frame after the frame immediately before the interruption of communication.

Specifically, for example, if communication fails immediately after the transmission of the image data D corresponding to frames having frame numbers 1, 2, and 3, the image data D corresponding to frames having the frame numbers 4 and 5 is stored in the storage unit 23. After the communication is reestablished such that the image data D corresponding to frames having the subsequent frame numbers 6 and higher can be transferred, the image data D corresponding to the frame having the frame number 4 is read from the storage unit 23 and transferred, and the image data D corresponding to the frame having the frame number 6 is stored in the storage unit 23.

Subsequently, the image data D corresponding to the frame having the frame number 5 is read from the storage unit 23 and transferred, and the image data D corresponding to the frame having the frame number 7 is stored in the storage unit 23. This results in simultaneous reading and storing of the image data D repeated at the storage unit 23, and thus a complicated process.

Instead of this complicated process, the image data D stored in the storage unit 23 due to a failure of transmission remains in the storage unit 23 even after the reestablishment of communication, and the image data D corresponding to the individual frames read upon the reestablishment of communication is transferred first. Upon completion of the transmission of the image data D of individual frames, the image data D of individual frames stored in the storage unit 23 can be transferred.

Specifically, as described in the example above, if the communication fails immediately after the transmission of the image data D of individual frames having the frame numbers 1, 2, and 3 and the communication is reestablished immediately after the image data D of individual frames having the frame numbers 4 and 5 are stored in the storage unit 23, the image data D of individual frames having the frame numbers 4 and 5 remains in the storage unit 23 while the image data D of individual frames having the frame numbers 6 and higher, which is read upon the reestablishment of communication, is transferred first. After completion of the transmission of the remaining image data D, the image data D of individual frames having the frame numbers 4 and 5 stored in the storage unit 23 can be transferred.

This precludes simultaneous reading and storing of the image data D repeated at the storage unit 23. Thus, after the completion of the transmission process of the image data D, the image data D stored in the storage unit 23 can be read and transferred. This simplifies the processes carried out at the radiographic image capturing device 1.

[Shifting in Order of Capturing and Transmission of Image Data D]

In the above-mentioned description, the frames of the image data D are transferred in the order of frame numbers 1, 2, 3, and 6 to the image processor 51. The frames of the image data D having frame numbers 4 and 5 are then transferred in this order. The order of transmission of the image data D to the image processor 51 differs from the order of capturing of the image data D.

Such a drawback can be prevented by, for example, instructing at least the control unit 22 of the radiographic image capturing device 1 to number the frames of the image data D read in the continuous radiographic mode in the order of capturing and writing the frame numbers in the headers of the image data D of the corresponding frames.

In this way, the image processor 51 can rearrange the received frames of the image data D in accordance with the frame numbers attached to the image data D (i.e., in the order of capturing).

The frames of the image data D stored in the storage unit 23 every time the communication intermittently fails can be numbered in the order of capturing so that the image processor 51 can rearrange the received frames of the image data D in the order of capturing.

Even if the order of transmission of the frames of the image data D to the image processor 51 differs from the order of capturing of the frames of the image data D at the radiographic image capturing device 1 due to an insufficient communication environment, the frames of the image data D can be appropriately rearranged in the order of capturing, and thus, processes such as identification and generation of radiographic images can be appropriately carried out.

[Remaining Memory in Storage Unit and Remaining Power in Internal Power Source]

In the case where the radiographic image capturing device 1 including the storage unit 23 and the internal power source 24, as illustrate in FIG. 2, sequentially reads the image data D of individual frames in the continuous radiographic mode, the number of frames that can be captured may be limited depending on the remaining memory in the storage unit 23 and/or the remaining power in the internal power source 24. In particular, moving image radiography may be disabled that requires the reading of the image data D corresponding to many frames for the generation of multiple radiographic images.

For example, in tomosynthetic radiography, the image data D corresponding to the number of frames required for the generation of ten to twenty radiographic images should be captured. In kymographic radiography of the lung, the image data D corresponding to even more frames should be captured.

The control unit 22 of the radiographic image capturing device 1 can monitor the remaining memory in the storage unit 23 and the remaining power in the internal power source 24 and announce a decrease in the memory and power below a predetermined value to the operator or radiologist with the indicator 28 (see FIG. 1) illuminated in a predetermined color or flashing pattern or with a beep sound, for example. In the case where the operator has access to a smart phone or a portable information terminal, the announcement may be transmitted to the smart phone or the portable information terminal such that the announcement is displayed on the screen or a specific sound is generated.

The maximum number of capturable frames is determined on the basis of the remaining memory of the storage unit 23, the remaining power of the internal power source 24, the electrical power required for reading of the image data D corresponding to a single frame, and the memory required for storing the image data D corresponding to a single frame. For example, the maximum time (seconds) of radiography available in the continuous radiographic mode and/or the availability of kymographic and tomosynthetic radiography can be determined. The determined information then can be announced by the indicator 28 illuminating or indicating a flashing pattern or with a beep sound or announced on a smart phone, for example.

It is preferred that the storage unit 23 storing the image data D includes a non-volatile storage medium, particularly in the continuous radiographic mode or during communication failure with an external unit. It is also preferred that the non-volatile storage medium be detachable from the radiographic image capturing device 1. The storage unit 23 provided in the form of a non-volatile storage medium detachable from the radiographic image capturing device 1 can be detached from the radiographic image capturing device 1 during communication failure with the external unit and connected to another external unit, to readily read the image data D stored in the storage unit 23.

For example, in dual-energy subtraction radiography, image data D corresponding to two radiographic images is usually captured at a significantly short time interval. Thus, the radiographic image capturing device 1 according to this embodiment can perform radiography in the moving image mode or the continuous radiographic mode.

The present invention is not limited to the above embodiments, and suitable modification is possible without leaving the scope of the invention.

This application is based upon and claims the benefit of priority from the prior Japanese Patent Application No. 2015-142809, filed Jul. 17, 2015, the entire contents of which are incorporated herein by reference.

What is claimed is:

1. A radiographic image capturing device comprising:
   a two-dimensional array of radiation detectors that generate electrical charges corresponding to a dose of incident radiation emitted from an irradiator; and
   a processor that reads the electrical charges discharged from the radiation detectors according to a manner which is prescribed by one of three radiographic modes which is set,
   wherein the three radiographic modes include:
   a still image mode in which the processor reads the electrical charges once in synchronization with an emission timing of the dose of incident radiation,
   a moving image mode in which the processor reads the electrical charges more than once in synchronization with an emission timing of the dose of incident radiation; and a continuous radiographic mode in which the processor sequentially reads the electrical charges more than once without synchronization with an emission timing of the dose of incident radiation.

2. The radiographic image capturing device according to claim 1, wherein, in a case in which an instruction for setting one of the three radiographic modes has not been received, the processor sets the continuous radiographic mode as the radio graphic mode, and, in the manner prescribed by the continuous radiographic mode, sequentially reads the electrical charges more than once without synchronization with an emission timing of the dose of incident radiation.

3. The radiographic image capturing device according to claim 1, wherein, in a case in which the continuous radiographic mode is set as the radiographic mode, the processor detects a start of the dose of incident radiation and starts reading the electrical charges upon start of the dose of incident radiation.

4. The radiographic image capturing device according to claim 1, wherein the processor sets the continuous radiographic mode as the radiographic mode and reads the electrical charges according to the manner prescribed by the continuous radiographic mode immediately after startup of the radiographic image capturing device.

5. A radiographic image capturing system comprising:
the radiographic image capturing device according to claim 1; and
an image processor which generates image data based on the electrical charges read by the processor of the radiographic image capturing device in the manner prescribed by one of the three radiographic modes which is set.

6. A radiographic image capturing system comprising:
the radiographic image capturing device according to claim 2; and
an image processor which generates image data based on the electrical charges read by the processor of the radiographic image capturing device in the manner prescribed by one of the three radiographic modes which is set.

7. A radiographic image capturing system comprising:
the radiographic image capturing device according to claim 4; and
an image processor which generates image data based on the electrical charges read by the processor of the radiographic image capturing device in the manner prescribed by one of the three radiographic modes which is set.

8. The radiographic image capturing device according to claim 1, wherein, in the continuous radiographic mode, the processor reads the electrical charges even at a timing which overlaps with a time during which the radiation detectors are being irradiated with incident radiation from the irradiator.

* * * * *